US011395738B2

(12) United States Patent
Benichou et al.

(10) Patent No.: US 11,395,738 B2
(45) Date of Patent: Jul. 26, 2022

(54) DOCKING ELEMENTS

(71) Applicant: TRULEAF MEDICAL LTD., Caesarea (IL)

(72) Inventors: Netanel Benichou, D.N. Hof Carmel (IL); Benjamin Spenser, D.N. Hof Carmel (IL); Moran Sobol, Haifa (IL)

(73) Assignee: TRULEAF MEDICAL LTD., Caesarea (IL)

( * ) Notice: Subject to any disclaimer, the term of this patent is extended or adjusted under 35 U.S.C. 154(b) by 0 days.

(21) Appl. No.: 16/580,319

(22) Filed: Sep. 24, 2019

(65) Prior Publication Data
US 2020/0093599 A1 Mar. 26, 2020

Related U.S. Application Data

(60) Provisional application No. 62/735,866, filed on Sep. 25, 2018.

(51) Int. Cl.
*A61F 2/24* (2006.01)
*A61F 2/00* (2006.01)

(52) U.S. Cl.
CPC .......... *A61F 2/2445* (2013.01); *A61F 2/0077* (2013.01); *A61F 2/2409* (2013.01);
(Continued)

(58) Field of Classification Search
CPC .... A61F 2/2445; A61F 2/0077; A61F 2/2409; A61F 2002/0086; A61F 2220/0016;
(Continued)

(56) References Cited

U.S. PATENT DOCUMENTS 7,291,168 B2 * 11/2007 Macoviak ............. A61F 2/2412
623/2.36
8,408,214 B2 4/2013 Spenser
(Continued)

FOREIGN PATENT DOCUMENTS

WO 2011/057087 A1 5/2011
WO 2015/173794 A1 11/2015
(Continued)

OTHER PUBLICATIONS

International Search Report and Written Opinion from PCT/IL2018/050229 dated May 9, 2018.
(Continued)

*Primary Examiner* — Yashita Sharma
*Assistant Examiner* — Jared Klar Rovira
(74) *Attorney, Agent, or Firm* — Sughrue Mion, PLLC

(57) ABSTRACT

Apparatus and methods are described for treating a subject with a diseased mitral valve. A docking element is implanted within the subject's left atrium such that no portion of the docking element extends through the subject's mitral valve. The docking element includes a ring having a smaller size than that of the subject's mitral annulus, and which configured to be implanted within 15 mm of the mitral annulus. A frame extends upwardly from the ring, a portion of the frame being configured to be disposed in a vicinity of the mitral annulus and to generate tissue ingrowth from the subject's atrial walls in the vicinity of the mitral annulus. A material disposed between the portion of the frame and the ring is configured to form a seal between atrial walls in the vicinity of the mitral annulus and the ring. Other applications are also described.

14 Claims, 21 Drawing Sheets

(52) U.S. Cl.
CPC ............... *A61F 2002/0086* (2013.01); *A61F 2220/0016* (2013.01)

(58) Field of Classification Search
CPC ...... A61F 2250/0031; A61F 2250/0051; A61F 2/2418; A61F 2220/0008; A61F 2250/001
See application file for complete search history.

(56) References Cited

U.S. PATENT DOCUMENTS

| | | | |
|---|---|---|---|
| 8,454,686 | B2 | 6/2013 | Alkhatib |
| 8,828,043 | B2 | 9/2014 | Chambers |
| 8,870,950 | B2 | 10/2014 | HaCohen |
| 8,888,843 | B2 | 11/2014 | Khairkhahan et al. |
| 8,992,604 | B2 | 3/2015 | Gross et al. |
| 9,011,515 | B2 | 4/2015 | Schweich, Jr. et al. |
| 9,017,399 | B2 | 4/2015 | Gross et al. |
| 9,241,792 | B2 | 1/2016 | Benichou et al. |
| 9,326,852 | B2 | 5/2016 | Spenser |
| 9,387,078 | B2 | 7/2016 | Gross et al. |
| 9,414,823 | B2 | 8/2016 | Ben Hamou et al. |
| 9,566,152 | B2 | 2/2017 | Schweich, Jr. et al. |
| 9,622,862 | B2 | 4/2017 | Lashinski et al. |
| 2004/0138745 | A1 | 7/2004 | Macoviak et al. |
| 2006/0052804 | A1 | 3/2006 | Miahle |
| 2007/0066993 | A1 | 3/2007 | Kreidler |
| 2007/0156233 | A1 | 7/2007 | Kapadia et al. |
| 2008/0208327 | A1 | 8/2008 | Rowe |
| 2008/0215085 | A1 | 9/2008 | Whisenant et al. |
| 2009/0281609 | A1 | 11/2009 | Benichou et al. |
| 2010/0049315 | A1 | 2/2010 | Kirson |
| 2010/0204785 | A1 | 8/2010 | Alkhatib |
| 2011/0071623 | A1 | 3/2011 | Finch et al. |
| 2011/0137410 | A1 | 6/2011 | Hacohen |
| 2011/0224785 | A1 | 9/2011 | Hacohen |
| 2012/0022633 | A1* | 1/2012 | Olson ................... A61F 2/2418 623/1.11 |
| 2012/0022639 | A1 | 1/2012 | Hacohen et al. |
| 2012/0022640 | A1 | 1/2012 | Gross et al. |
| 2012/0083832 | A1 | 4/2012 | Delaloye et al. |
| 2012/0253386 | A1 | 10/2012 | Rowe et al. |
| 2013/0006352 | A1 | 1/2013 | Yaron |
| 2013/0035759 | A1 | 2/2013 | Gross et al. |
| 2014/0025164 | A1 | 1/2014 | Montorfano et al. |
| 2014/0031928 | A1 | 1/2014 | Murphy et al. |
| 2014/0207231 | A1 | 7/2014 | Hacohen et al. |
| 2014/0222136 | A1 | 8/2014 | Geist et al. |
| 2014/0243966 | A1 | 8/2014 | Garde et al. |
| 2014/0277390 | A1 | 9/2014 | Ratz et al. |
| 2014/0309730 | A1 | 10/2014 | Alon et al. |
| 2014/0324164 | A1 | 10/2014 | Gross et al. |
| 2014/0358222 | A1 | 12/2014 | Gorman, III et al. |
| 2014/0379074 | A1 | 12/2014 | Spence et al. |
| 2015/0045880 | A1 | 2/2015 | Hacohen |
| 2015/0157457 | A1 | 6/2015 | Hacohen |
| 2015/0173898 | A1 | 6/2015 | Drasler et al. |
| 2015/0209136 | A1* | 7/2015 | Braido ................... A61F 2/2403 623/2.18 |
| 2015/0216661 | A1 | 8/2015 | HaCohen et al. |
| 2015/0351906 | A1 | 12/2015 | Hammer et al. |
| 2015/0359629 | A1 | 12/2015 | Ganesan et al. |
| 2016/0106539 | A1 | 4/2016 | Buchbinder et al. |
| 2016/0213473 | A1 | 7/2016 | Hacohen et al. |
| 2016/0242905 | A1 | 8/2016 | Chambers |
| 2016/0296330 | A1 | 10/2016 | Hacohen |
| 2016/0302920 | A1 | 10/2016 | Al-Jilaihawi |
| 2016/0310274 | A1 | 10/2016 | Gross et al. |
| 2016/0324633 | A1 | 11/2016 | Gross et al. |
| 2016/0346084 | A1 | 12/2016 | Taylor et al. |
| 2016/0367365 | A1 | 12/2016 | Conklin |
| 2018/0042719 | A1 | 2/2018 | Chambers et al. |
| 2018/0042720 | A1 | 2/2018 | Chambers |
| 2018/0042721 | A1 | 2/2018 | Chambers |
| 2018/0133009 | A1* | 5/2018 | Alon ..................... A61F 2/2466 |
| 2018/0168804 | A1* | 6/2018 | Nguyen ................... D03D 3/02 |
| 2018/0200049 | A1 | 7/2018 | Chambers et al. |
| 2018/0206988 | A1 | 7/2018 | Chambers |
| 2018/0256329 | A1 | 9/2018 | Chambers et al. |
| 2018/0360602 | A1 | 12/2018 | Kumar |
| 2019/0167409 | A1 | 6/2019 | Genereux |
| 2019/0175111 | A1 | 6/2019 | Genereux et al. |
| 2019/0201192 | A1 | 7/2019 | Kruse et al. |
| 2019/0209320 | A1 | 7/2019 | Drasler et al. |
| 2019/0216597 | A1 | 7/2019 | Chambers |
| 2019/0247191 | A1 | 8/2019 | Chambers et al. |
| 2019/0365538 | A1 | 12/2019 | Chambers et al. |

FOREIGN PATENT DOCUMENTS

| | | |
|---|---|---|
| WO | 2015/188066 A1 | 12/2015 |
| WO | 2016/134239 A1 | 8/2016 |
| WO | 2018/031855 A1 | 2/2018 |
| WO | 2018/031857 A1 | 2/2018 |
| WO | 2018/031862 A1 | 2/2018 |
| WO | 2018/136726 A1 | 7/2018 |
| WO | 2018/140374 A1 | 8/2018 |
| WO | 2018/165225 A1 | 9/2018 |
| WO | 2018/178966 A1 | 10/2018 |
| WO | 2018/232118 A1 | 12/2018 |
| WO | 2019/112983 A1 | 6/2019 |
| WO | 2019/112985 A1 | 6/2019 |
| WO | 2019/136040 A1 | 7/2019 |
| WO | 2019/157480 A1 | 8/2019 |
| WO | 2021/064624 A1 | 4/2021 |

OTHER PUBLICATIONS

International Search Report and Written Opinion from PCT/IL2018/050230 dated May 22, 2018.
Preston-Maher, et al.; "A Technical Review of Minimally Invasive Mitral Valve Replacements", Cardiovascular Engineering and Technology, 2015, vol. 6, No. 2, pp. 174-184.
Extended European Search Report issued for EP 19199161.1 dated Dec. 4, 2019.
Cismaru, et al., "Distance between the Left Atrial Appendage and Mitral Annulus Evaluated by CARTO 3 Integrated Computed Tomography Imaging", Medical Principles and Practice, Oct. 2015, 24(6): 555-559. (Year: 2015).
Invitation to pay Additional Fees for PCT Application No. PCT/IB2020/059195 dated Dec. 14, 2020.
International Search Report and Written Opinion for PCT Application No. PCT/IB2020/059195 dated Feb. 4, 2021.
A Restriction Requirement dated Feb. 10, 2021 for U.S. Appl. No. 16/498,065.
An Office Action dated Apr. 27, 2021 for U.S. Appl. No. 16/498,065.

* cited by examiner

DOCKING ELEMENTS

CROSS-REFERENCE TO RELATED APPLICATIONS

The present application claims priority from U.S. Provisional application 62/735,866 to Benichou et al., entitled "Docking elements," filed Sep. 25, 2018, which is incorporated herein by reference.

FIELD OF EMBODIMENTS OF THE INVENTION

Some applications of the present invention generally relate to medical apparatus and methods. Specifically, some applications of the present invention relate to apparatus and methods for use with a prosthetic mitral valve.

BACKGROUND

Atrioventricular valves are cardiac valves that prevent backflow from the ventricles into the atria during systole. They are anchored to the wall of the heart at the fibrous skeleton by anchoring tendons named chordae tendineae. The chordae tendineae are attached to papillary muscles. Together, the papillary muscles and the chordae tendineae keep the valves from prolapsing into the atria when they close during systole. The actual opening and closing of the valves is caused by a pressure gradient across the valve. The left-side atrioventricular valve is a bicuspid valve having two leaflets, and is commonly known as the mitral valve. The right-side atrioventricular valve is a tricuspid valve, having three leaflets. Both of these valves may be damaged and dysfunctional, resulting in leakage during systole, requiring the valves to be repaired or replaced.

While the mitral valve is generally an ellipse or D-shaped, the tricuspid valve is more circular. The left ventricle pumps oxygenated blood around the body and so the mitral valve has to withstand a higher pressure than the tricuspid valve which only has to pump deoxygenated blood to the nearby lungs.

Occasionally, the mitral valve is congenitally abnormal or destroyed by infection or a bacterial endocarditis. More often, the mitral valve becomes degenerative with age, or as a result of rheumatic fever. There are different valvular heart disorders associated with the mitral valve such as mitral stenosis and mitral regurgitation. In the case of mitral stenosis, the valve orifice, i.e., the cross-section available for blood passage is reduced because of calcium nodes, leaflet thickening and/or reduced leaflet mobility, and, consequently, the valve does not allow normal blood flow. To overcome the damaged valve and to transport the same amount of blood, the left atrium requires a higher pressure than normal. The constant pressure overload of the left atrium may cause it to increase in size and become more prone to develop atrial fibrillation and to lose the atrial kick. The loss of the atrial kick due to atrial fibrillation can cause a precipitous decrease in cardiac output. A reduction in cardiac output, associated with acceleration of heart rate and shortening of the diastolic time, frequently leads to congestive heart failure. In most cases, mitral stenosis is due to rheumatic heart disease. The treatment options for mitral stenosis include medical management, surgical repair, surgical replacement of the valve, and percutaneous balloon valvuloplasty.

Mitral regurgitation causes heart murmurs and may have severe physiological consequences. Mitral regurgitation is caused either by ischemic heart disease (such cases being called "ischemic mitral regurgitation"), or mitral valve prolapse. Ischemic mitral regurgitation is a result of ventricular remodeling which is secondary to ischemic heart disease. The heart's posterior wall, which is not attached to the heart's fibrous skeleton, dilates. As a result of the change of the left ventricular geometry, the posterior leaflet, which is attached to the posterior heart wall, is displaced and misaligned from the anterior leaflet which results in mitral regurgitation.

Mitral valve prolapse is a condition caused by degeneration of the valve's connective tissue. Patients with classic mitral valve prolapse have surplus connective tissue. This weakens the leaflets and adjacent tissue, resulting in increased leaflet area and elongation of the chordae tendineae. Elongation of the chordae tendineae often causes rupture. Tweaked leaflets may be displaced in some portion of one or both of the abnormally thickened mitral valve leaflets into the left atrium during systole. Advanced lesions lead to leaflet folding, inversion, and displacement toward the left atrium. The abnormal leaflet structure leads to incomplete closure of the mitral valve and consequent mitral regurgitation.

In mitral regurgitation, the heart has to work harder by pumping not only the regular volume of blood, but also the extra volume of blood that is regurgitated back into the left atrium. The added workload creates an excessive strain on the left ventricle, which can lead to heart failure.

While patients with mild to moderate mitral regurgitation caused by mitral valve prolapse might experience no symptoms, increasing severity, even without symptoms, increases the load on the left ventricle. Over time this can result in ventricular dilatation and congestive heart failure.

Mitral valve disease is conventionally treated by open heart surgery; either by surgical repair, which is usually performed using an annuloplasty ring, or by surgical replacement with a valve prosthesis. In some cases, such as when the valve is too damaged, mitral valves may require replacement. Mitral valve replacement may be performed robotically or manually. Surgical valve replacement or repair is often a demanding operation as it requires cardiopulmonary bypass and it can expose patients, especially elderly ones, to many risks.

A large variety of percutaneous or transcutaneous medical procedures are currently being developed and/or practiced. For example, transcatheter procedures are known for replacement of aortic and pulmonary heart valves. These procedures, which are performed under local anesthesia in the cardiac catheterization lab, rather than by cardiac surgery, offer benefits to these patients. According to such approaches, the valve is inserted on a delivery device similar to a catheter or a sheath and then implanted in the desired location via access through a large blood vessel such as the femoral artery, for example. This involves making a very small perforation in the patient's skin, such as in the groin area, in order to access the femoral artery. This minimally invasive option is usually safer than open heart surgery, and recovery times are typically shorter.

SUMMARY OF EMBODIMENTS

In accordance with some applications of the present invention, a docking element is placed within a subject's left atrium, such that no portion of the docking element extends through the subject's mitral valve. Typically, the docking element includes a frame and a ring coupled to the frame. Typically, the frame is made of a shape memory material (e.g., a shape memory alloy, such as nitinol), that is cut to and shape set such as to define a plurality of cells defined by struts of the shape memory material. Typically, a portion of the frame that is closest to the ring is covered in a skirt of a material that facilitates tissue ingrowth to the frame. For example, the skirt may be made of a fabric such as PET, PTFE, and/or nylon, and may be coupled to the outside of the frame and/or the ring using stitches. Typically, the portion of the frame that is configured to be disposed in the vicinity of the mitral annulus (e.g., at the mitral annulus and/or starting slightly above the mitral annulus (e.g., within 15 mm of the mitral annulus)) is covered with the skirt. For some applications, the skirt is configured to be disposed from between 1 mm and 2 mm above the mitral valve annulus until a height of between 15 mm and 20 mm above the mitral valve annulus. For some applications, tissue-ingrowth elements are coupled to the skirt to encourage tissue ingrowth. For some applications, the skirt extends from the ring to a height on the frame of at least 5 mm (e.g., at least 10 mm), and/or less than 25 mm (e.g., less than 20 mm), e.g., between 5 and 25 mm, or between 10 and 20 mm. For some applications, from where the skirt terminates (i.e., from the upper end of the skirt), struts of the frame are covered in sleeves of a material that is typically the same as the material from which skirt is made. The sleeves of material are configured to encourage tissue ingrowth to the struts of the frame. Typically, at junctions between struts the sleeves are stitched together. For some applications, the docking element is deployed in the left atrium, such that the frame extends to the roof of the left atrium.

Typically, the docking element becomes anchored to the subject's heart by virtue of tissue ingrowth to the portion of the frame that is disposed in the vicinity of the mitral annulus (e.g., at the mitral annulus, and/or slightly above (e.g., within 15 mm of) the mitral annulus)) and is covered with the skirt, and/or tissue ingrowth from the left atrium wall to the struts of the frame that are covered with the sleeves. Typically, prior to the tissue ingrowth having occurred, the docking element is anchored in place within the left atrium by virtue of the frame expanding such as to contact the walls and the roof of the left atrium. Further typically, the expansion of the frame such as to contact the walls and the roof of the left atrium would not provide sufficient support to anchor the docking element in place within the left atrium, once the prosthetic mitral valve apparatus is placed inside the docking element, such that the docking element is exposed to left ventricular blood pressure being exerted upon the prosthetic mitral valve leaflets.

Therefore, prior to the implantation of the prosthetic mitral valve apparatus, the docking element is left in place within the left atrium, such as to allow sufficient tissue ingrowth to occur, prior to implantation of the prosthetic mitral valve apparatus. Typically, the docking element is configured such that, when the prosthetic mitral valve apparatus is implanted, the anchoring of the docking element within the left atrium is primarily via the tissue ingrowth to the docking element. Typically, the mitral annulus is able to bear a higher load than other portions of the left atrial walls. Therefore, for some applications, the docking element is configured such that, when the prosthetic mitral valve apparatus is implanted, the anchoring of the docking element within the left atrium is primarily via the tissue ingrowth from the atrial walls in the vicinity of the mitral annulus to the docking element. For example, by virtue of the docking element including the skirt (which is configured to be disposed in the vicinity of the mitral annulus, e.g., at the mitral annulus or slightly above the mitral annulus (e.g., as described hereinabove)), the docking element may be configured to encourage greater tissue ingrowth in the vicinity of the mitral annulus than at other portions of the frame.

Typically, the docking element is configured to facilitate anchoring of prosthetic mitral valve apparatus to the subject's mitral valve. For some applications, the docking element occupies some of the area defined by the native mitral annulus. For example, it is typically the case that the skirt occupies some of the space between (a) the location at which the frame becomes anchored to the atrial walls in the vicinity of the native mitral annulus (by virtue of tissue ingrowth to the skirt and/or the frame itself) and (b) the ring. That is to say that the docking element typically includes (a) the ring (within which the prosthetic valve apparatus is anchored), and (b) a portion of the frame that is covered with the skirt, such as to encourage tissue ingrowth from the atrial walls in the vicinity of the mitral annulus to that portion. Typically, the size of the ring (e.g., the outer perimeter of the ring) is smaller than the size of the portion of the frame into which there is the tissue ingrowth (e.g., the inner perimeter of the portion of the frame). Further typically, there is a material (e.g., a fabric) that bridges between the ring and the portion of the frame into which there is the tissue ingrowth. For some applications, the material that bridges between the ring and the portion of the frame into which there is tissue ingrowth is a portion of the skirt.

For some applications, a mitral annulus repair device is implanted in a subject suffering from mitral valve regurgitation, in which there is backflow of blood from the left ventricle to the left atrium during systole, due to the mitral valve leaflets not fully closing. Typically, the mitral annulus repair device is generally similar to the docking element described hereinabove. However, for some applications, in place of a ring that is configured to anchor a prosthetic mitral valve apparatus, the mitral annulus repair device includes an adjustable or self-adjusting ring. Rather than being used to support a prosthetic mitral valve apparatus, the adjustable ring is configured to decrease the area of the mitral annulus, by the diameter of the ring decreasing by being adjusted (e.g., via cinching), or self-adjusting, subsequent to tissue ingrowth having occurred.

Typically, prior to the diameter of the ring decreasing, the mitral annulus repair device is left in place within the left atrium, such as to allow tissue ingrowth to occur. Typically, the mitral annulus repair device is configured such that, when the diameter of the ring is decreased, the anchoring of the mitral annulus repair device within the left atrium is primarily via the tissue ingrowth to the mitral annulus repair device. For some applications, the mitral annulus repair device is configured such that, when the diameter of the ring is decreased, the anchoring of the mitral annulus repair device within the left atrium is primarily via the tissue ingrowth from the atrial walls in the vicinity of the mitral annulus to the mitral annulus repair device. For example, by virtue of the mitral annulus repair device including the skirt (which is configured to be disposed in the vicinity of the mitral annulus (e.g., at the mitral annulus, and/or or slightly above the native mitral annulus (e.g., as described hereinabove)), the mitral annulus repair device may be configured to encourage greater tissue ingrowth in the vicinity of the mitral annulus than at other portions of the frame.

Typically, once sufficient tissue ingrowth has occurred, the diameter of the ring is decreased by being adjusted (e.g., via cinching), or self-adjusting. Typically, since the atrial walls in the vicinity of the mitral annulus has undergone tissue ingrowth with respect to the mitral annulus repair device, decreasing the diameter of the ring remodels the heart, by reducing the size of the mitral annulus. In turn, the mitral leaflets are brought closer to each other and mitral valve regurgitation is reduced or eliminated. It is noted that, for some applications, there isn't substantial tissue ingrowth with respect to the ring of the mitral annulus repair device. Rather, most of the tissue ingrowth is with respect to the frame and/or the skirt of the mitral annulus repair device. Nevertheless, since the ring is coupled to the frame and/or the skirt and there is tissue ingrowth with respect to the frame, the reduction in the diameter of the ring causes a reduction in the size of the mitral annulus.

For some applications, a mitral annulus device that includes an adjustable ring (as described hereinabove) is used in conjunction with a prosthetic mitral valve apparatus. For example, the ring may be adjusted such as to accommodate a prosthetic mitral valve apparatus having a given desired diameter.

There is therefore provided, in accordance with some applications of the present invention, apparatus for treating a subject with a diseased mitral valve, the apparatus including:

a docking element configured to be implanted within a left atrium of the subject such that no portion of the docking element extends through the subject's mitral valve, the docking element including:
  a ring configured to be implanted within 15 mm of a native mitral annulus of the subject, a size of the ring being smaller than a size of the subject's native mitral annulus;
  a frame extending upwardly from the ring,
    a portion of the frame being configured to be disposed in a vicinity of the subject's native mitral annulus and to generate tissue ingrowth to the docking element from atrial walls of the subject at least in the vicinity of the subject's native mitral annulus, and
    the frame being configured to anchor the docking element within the left atrium, prior to the tissue ingrowth to the docking element occurring, by the frame expanding against inner walls and a roof of the left atrium; and a material disposed between the portion of the frame and the ring, the material being configured to form a seal between atrial walls in the vicinity of the native mitral annulus, and the ring; and
  a prosthetic mitral valve apparatus configured:
  subsequent to the ingrowth of the tissue of the left atrium to the portion of the frame having occurred, to be placed at least partially inside the docking element, and
  to become anchored to the docking element, at least partially by radially expanding against the ring.

In some applications, the frame does not include additional anchoring portions for anchoring to any additional portions of the subject's body other than the walls and the roof of the left atrium.

In some applications, the ring includes an outer portion that includes a fabric hollow torus, and an inner portion that includes an element selected from the group consisting of: an elastic material, and a spring.

In some applications, the ring is configured to be adjustable in size.

In some applications, the apparatus is for use with a balloon, the prosthetic mitral valve apparatus includes a balloon-expandable prosthetic mitral valve apparatus configured to be radially expanded by the balloon, and the ring includes an elastic ring that is configured:
  to define a given diameter when the ring is not subjected to any forces,
  to expand to a second diameter to allow the balloon-expandable prosthetic mitral valve apparatus to be expanded by the balloon,
  to undergo a reduction in diameter that is at least similar to a reduction in diameter that the prosthetic mitral valve apparatus undergoes due to recoiling after the balloon is deflated, and
  after undergoing the expansion and reduction in diameter, to exert sufficient radial force on the prosthetic mitral valve apparatus to anchor it in place even during left ventricular systole.

In some applications, the frame includes a plurality of struts that define a plurality of cells, and wherein the material includes a fabric skirt that is configured to cover a portion of the frame extending from the ring until a height of at least 5 mm from the ring.

In some applications, when the frame is in a deployed state inside the left atrium, be cells are configured to define open areas of at least 3 square cm.

In some applications, the ring is configured to automatically adjust its size.

In some applications, the ring includes a fabric hollow torus, with a spring and a biodegradable material dispose therein such that the biodegradable material holds the spring in an expanded configuration, and the ring is configured to be automatically adjustable in size by the biodegradable material becoming degraded, and radial forces of the spring exerting a radially inward force on the torus.

In some applications:
  the docking element is configured to be placed into the subject's left atrium, via an interatrial septum of the subject, by advancing the docking element in a lateral direction with respect to the left atrium, along a longitudinal axis of the frame; and
  the ring is disposed laterally with respect to the frame, such that the ring is substantially parallel with the longitudinal axis of the frame.

In some applications, the docking element is configured to be deployed within the subject's left atrium, such that the longitudinal axis of the frame is substantially parallel to the subject's native mitral annulus.

In some applications, the frame includes a plurality of struts that define a plurality of cells, and wherein, within at least a portion of the frame, the struts of the frame are covered with fabric sleeves.

In some applications, at junctions between the struts that are covered with the fabric sleeves, adjacent fabric sleeves are stitched to each other.

There is further provided, in accordance with some applications of the present invention, a method for treating a subject with a diseased mitral valve, the method including:
  inserting a docking element into a left atrium of the subject, the docking element including a ring, and a frame extending from the ring;
  deploying the docking element within the subject's left atrium, such that:
    no portion of the docking element extends through the subject's mitral valve,
    the ring is disposed within 15 mm of a mitral valve annulus of the subject,
    a size of the ring is smaller than a size of the native mitral annulus,
    a portion of the frame is disposed in a vicinity of a native mitral annulus of the subject, and the portion of the frame is configured to generate tissue ingrowth to the docking element from atrial walls of the subject at least in the vicinity of the subject's native mitral annulus, the frame anchors the docking element within the left atrium, prior to the tissue ingrowth to the docking element occurring, by the frame expanding against inner walls and a roof of the left atrium, and a material is disposed between the portion of the frame and the ring, the material being configured to form a seal between atrial walls in the vicinity of the native mitral annulus and the ring;

inserting a prosthetic mitral valve apparatus to inside the ring; and causing the prosthetic mitral valve apparatus to radially expand against the ring, such that the prosthetic mitral valve apparatus is anchored within the ring.

There is further provided, in accordance with some applications of the present invention, apparatus for treating a subject with a diseased mitral valve, the apparatus including:

a mitral annulus repair device configured to be implanted within a left atrium of the subject such that no portion of the mitral annulus repair device extends through the subject's mitral valve, the mitral annulus repair device being configured to generate ingrowth of the tissue of the subject to the mitral annulus repair device, the mitral annulus repair device including:

a ring configured to be implanted within 5 mm of a native mitral annulus of the subject; and a frame extending upwardly from the ring, the frame being configured to anchor the mitral annulus repair device within the left atrium, prior to the tissue ingrowth to the mitral annulus repair device occurring, by the frame expanding against inner walls and a roof of the left atrium, the ring being adjustable in size and the ring being configured to reduce a diameter of the subject's native mitral annulus by a diameter of the ring being reduced, subsequent to tissue ingrowth to the mitral annulus repair device having occurred.

In some applications, wherein the mitral annulus repair device is configured, such that:

there is not substantial tissue ingrowth with respect to the ring, there is substantial ingrowth with respect to a first portion of the frame, and the ring is configured to reduce the diameter of the mitral annulus by reducing a diameter of a second portion of the frame to which the ring is coupled, and the second portion of the frame causing the first portion of the frame to reduce the diameter of the mitral annulus.

In some applications, the frame includes a plurality of struts that define a plurality of cells, wherein the first portion of the frame extends from the ring until a height of at least 5 mm from the ring and the first portion of the frame is covered in a fabric skirt that is configured to encourage tissue ingrowth thereto. In some applications, the cells defined by the struts define open areas of at least 3 square cm.

In some applications, the ring is configured to be manually adjustable in size.

In some applications, the ring includes a fabric hollow torus, with a string disposed therein, and ring is configured to be manually adjustable in size by an operator pulling a portion of the string.

In some applications, the ring is configured to automatically adjust its size.

In some applications, the ring includes a fabric hollow torus, with a spring and a biodegradable material disposed therein such that the biodegradable material holds the spring in an expanded configuration, and the ring is configured to be automatically adjustable in size by the biodegradable material becoming degraded, and radial forces of the spring exerting a radially inward force on the torus.

In some applications:

the mitral annulus repair device is configured to be placed into the subject's left atrium, via an interatrial septum of the subject, by advancing the mitral annulus repair device in a lateral direction with respect to the left atrium, along a longitudinal axis of the frame; and the ring is disposed laterally with respect to the frame, such that the ring is substantially parallel with the longitudinal axis of the frame.

In some applications, the mitral annulus repair device is configured to be deployed within the subject's left atrium, such that the longitudinal axis of the frame is substantially parallel to the subject's mitral annulus.

In some applications, the frame includes a plurality of struts that define a plurality of cells, and within at least a portion of the frame, the straits of the frame are covered with fabric sleeves.

In some applications, at junctions between the struts that are covered with the fabric sleeves, adjacent fabric sleeves are stitched to each other.

In some applications, the frame does not include additional anchoring portions for anchoring to any additional portions of the subject's body other than the walls and the roof of the left atrium.

There is further provided, in accordance with some applications of the present invention, a method for treating a subject with a diseased mitral valve, the method including:

inserting a mitral annulus repair device into a left atrium of the subject, the mitral annulus repair device including a ring, and a frame extending from the ring;

deploying the docking element within the subject's left atrium, such that (a) no portion of the a mitral annulus repair device extends through the subject's mitral valve, (b) the ring is disposed within 15 mm of a native mitral annulus of the subject, and (c) the frame anchors the mitral annulus repair device within the left atrium by the frame expanding against inner walls and a roof of the left atrium;

causing there to be tissue ingrowth with respect to the material, by leaving the mitral annulus repair device within the subject's left atrium; and subsequent to tissue ingrowth having occurred with respect to the material, causing a diameter of the subject's native mitral annulus to become reduced by the diameter of the ring becoming reduced.

The present invention will be more fully understood from the following detailed description of embodiments thereof, taken together with the drawings, in which:

DETAILED DESCRIPTION OF EMBODIMENTS

Figure 1A:
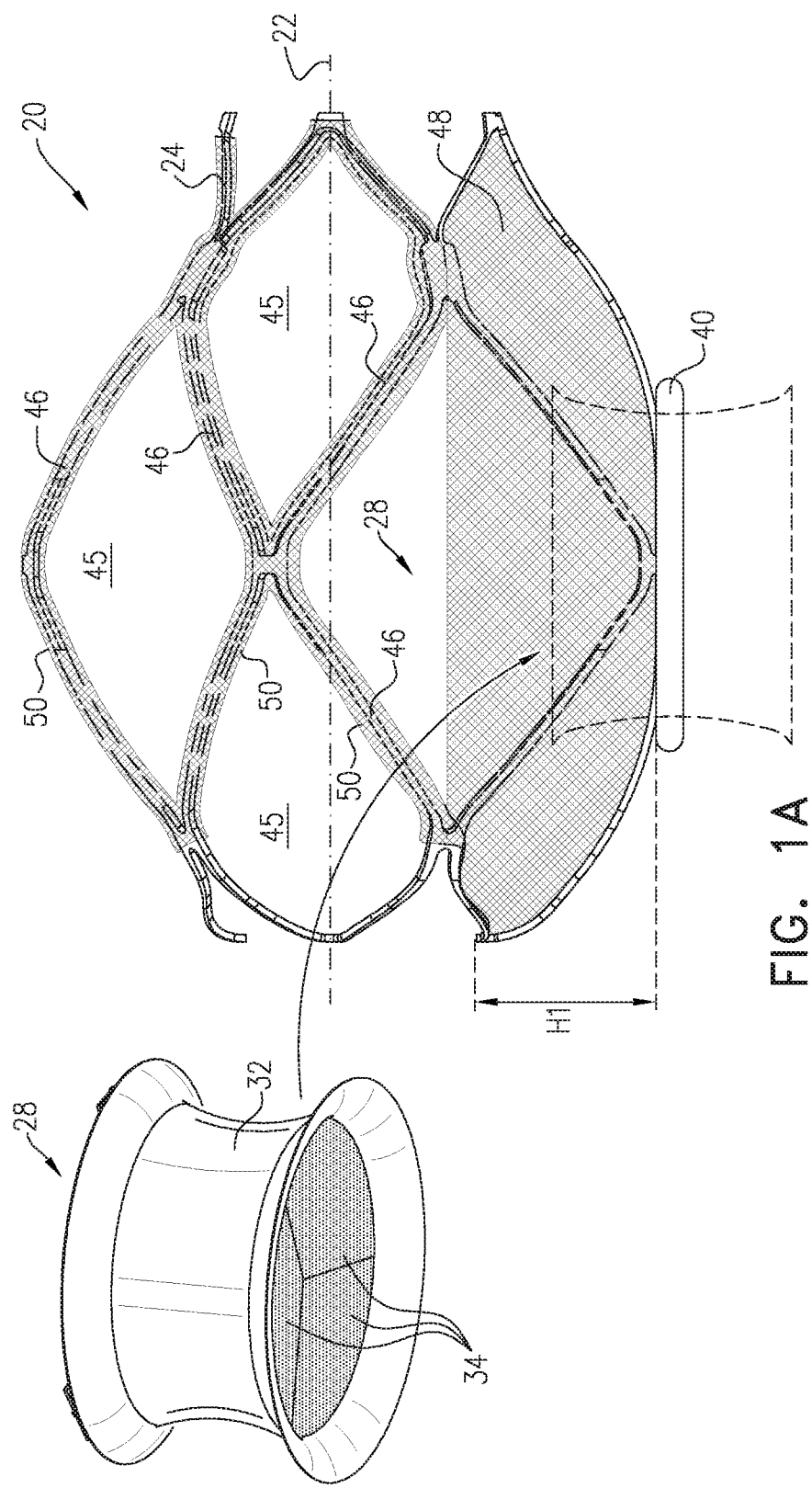
FIGS. 1A, 1B, and 1C are schematic illustrations of a docking element configured to facilitate anchoring of prosthetic mitral valve apparatus to a subject's mitral valve, in accordance with some applications of the present invention.
Figure 1B:
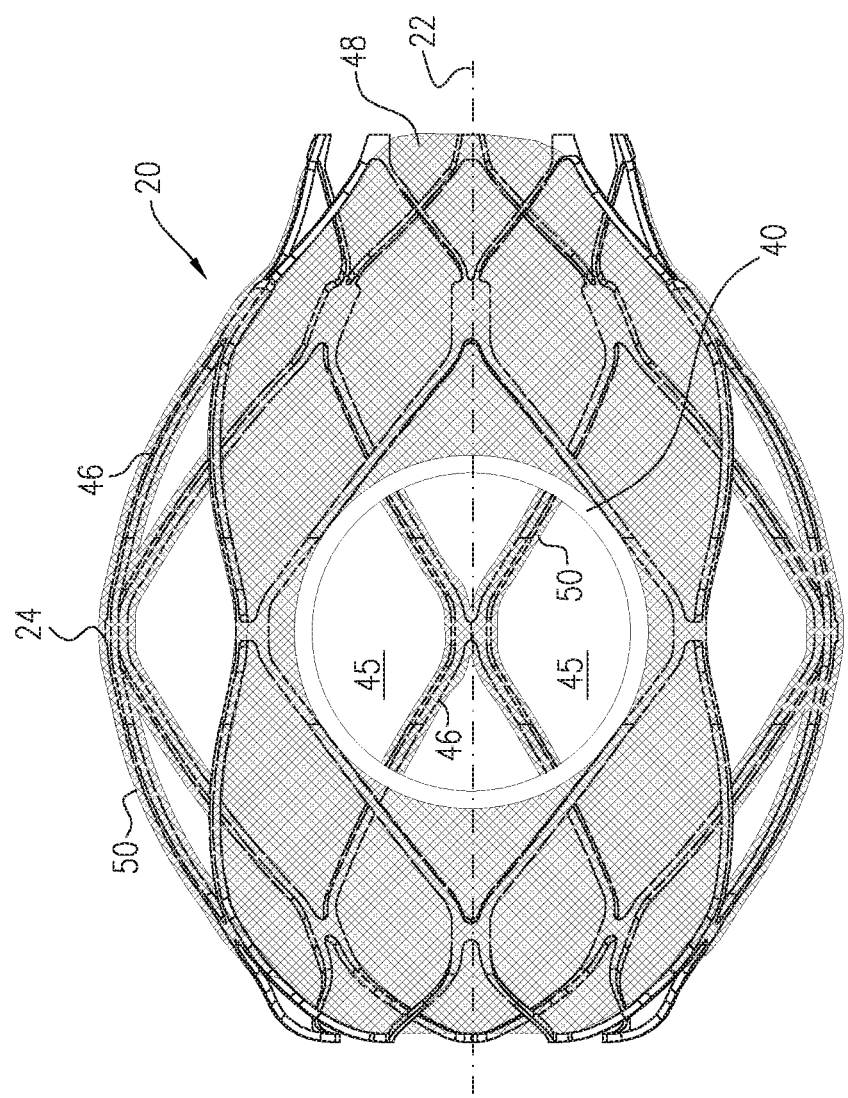
Figure 1C:
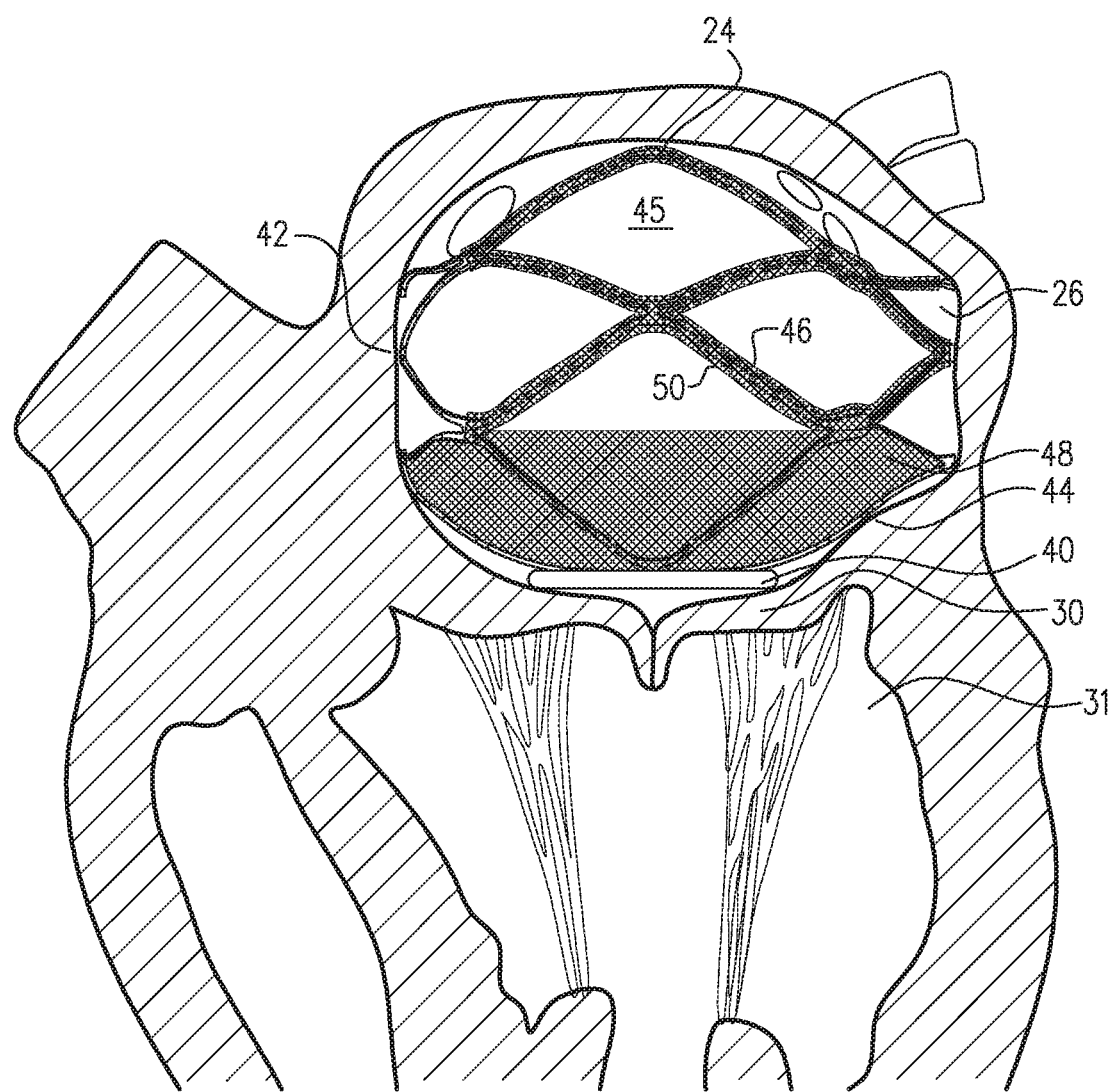

Reference is now made to FIGS. 1A, 1B, and 1C, which are schematic illustrations of a docking element 20, in accordance with some applications of the present invention. FIG. 1A shows a side view of the docking element, and FIG. 19 shows a view of the docking element that is rotated through 90 degrees around a longitudinal axis 22 of a frame 24 of the docking element relative to the view shown in FIG. 1A. Docking element is typically configured to facilitate anchoring of a prosthetic mitral valve apparatus 28 (shown in FIG. 1A) to a subject's mitral valve. FIG. 1C shows the docking element deployed inside a subject's left atrium 26, prior to the prosthetic mitral valve apparatus having been placed inside the docking element. As shown, in this state the native mitral valve leaflets 30 are still in place. The docking element is disposed, in its entirety, within the left atrium 26, and does not protrude into left ventricle 31.

Typically, the prosthetic mitral valve apparatus is a stented valve that comprises a stented frame 32 that is configured to support prosthetic valve leaflets 34. The prosthetic mitral valve apparatus is typically implanted within the native mitral valve of a subject with a diseased native valve, and the prosthetic valve leaflets function such as to replace the functioning of the native valve leaflets. Typically, the prosthetic valve leaflets are configured to act as a one-way valve, whereby in their open positions with respect to one another the leaflets allow flow to pass through the prosthetic valve apparatus from the inlet (on the atrial side) to the outlet (on the ventricular side), whereas reverse flow is prevented due to collapsible slack portions of the valve leaflets collapsing inwardly to block the reverse flow.

Typically, docking element 20 is implanted within the left atrium more than one week, or more than one month, before the implantation of the prosthetic mitral valve apparatus. Subsequent to the implantation of the docking element, and before the implantation of the prosthetic mitral valve apparatus, the anchoring of the docking element is typically strengthened by virtue of tissue ingrowth that occurs around the docking element, e.g., as described hereinbelow. Typically, no portion of the docking element extends through the subject's native mitral valve. Further typically, by virtue of the fact that no portion of the docking element extends through the subject's native mitral valve, the native mitral valve leaflets are able to continue functioning in their normal manner subsequent to the implantation of the docking element, and prior to the implantation of the prosthetic mitral valve apparatus.

For some applications, the docking element includes frame 24 and a ring 40 coupled to the frame. Ring 40 is described in further detail hereinbelow. Typically, in its deployed state inside the left atrium, the ring is disposed transversely with respect to the frame, such that a plane defined by the ring is substantially parallel to the longitudinal axis of the frame.

For some applications, the docking element is placed into left atrium 26, via interatrial septum 42 (shown in FIG. 1C), by advancing the docking element, along its longitudinal axis, in a lateral direction with respect to the subject's left atrium. Subsequently, substantially without rotating the longitudinal axis of the docking element, the docking element is deployed within the subject's left atrium, such that ring 40 is disposed in the vicinity of mitral annulus 44 (e.g., at the mitral annulus, and/or slightly above (e.g., as described hereinabove)), and is disposed transversely with respect to the frame. (It is noted that in some cases the frame may be rotated around the longitudinal axis, and/or there may be a small amount of rotation of the longitudinal axis itself, in order to align the ring with the native mitral valve annulus.) Thus, even in the deployed state of the docking element, the longitudinal axis of the frame is substantially parallel to a plane defined by the subject's mitral annulus. By virtue of the docking element deploying in this manner, the longitudinal axis of the docking element does not need to be substantially rotated with respect to the left atrium between being transseptally inserted into the left atrium, and being deployed within the left atrium. By contrast, if the ring was disposed at a longitudinal end of the frame such that the plane defined by the ring was substantially perpendicular to the longitudinal axis of the frame, this would make it challenging to insert the docking element transseptally. This is because the longitudinal axis of the docking element would need to be rotated (approximately 90 degrees relative to the interatrial septum) and released from the delivery device within the relatively small volume that is defined by the left atrium.

Typically, frame 24 is made of a self-expandable, shape memory material (e.g., a shape memory alloy, such as nitinol), that is cut to and shape set such as to define a plurality of cells 45 defined by struts 46 of the shape memory material. Alternatively or additionally, the frame is assembled from wires that are made of a self-expandable, shape memory material (e.g., a shape memory alloy, such as nitinol). Typically, a portion of the frame that is closest to the ring is covered in a skirt 48 of a material that facilitates tissue ingrowth to the frame. For example, the skirt may be made of a fabric such as PET, PTFE, and/or nylon, and may be coupled to the outside of the frame and/or the ring using stitches. Typically, the portion of the frame that is configured to be disposed in the vicinity of the mitral annulus (e.g., at the mitral annulus, and/or slightly above (e.g., within 15 mm of) the mitral annulus)) is covered with the skirt. For some applications, the skirt is configured to be disposed from between 1 mm and 2 mm above the mitral valve annulus until a height of between 15 mm and 20 mm above the mitral valve annulus. For some applications (not shown), tissue-ingrowth elements are coupled to the skirt to encourage tissue ingrowth. For example, such tissue-ingrowth elements may include hooks or loops (e.g., similar to those used in hook-and-loop fasteners), barbs, clips, pins, etc. For some applications, the skirt extends from the ring to a height H1 on the frame of at least 5 mm (e.g., at least 10 mm), and/or less than 25 mm (e.g., less than 20 mm), e.g., between 5 and 25 mm, or between 10 and 20 mm. For some applications, from where the skirt terminates (i.e., from the upper end of the skirt), struts of the frame are covered in sleeves 50 of a material that is typically the same as the material from which skirt 48 is made. The sleeves of material are configured to encourage tissue ingrowth to the struts of the frame. Typically, at junctions between struts the sleeves are stitched together. For some applications, the docking element is deployed in the left atrium, such that frame 24 extends to the roof of the left atrium.

Typically, docking element 20 becomes anchored to the subject's heart by virtue of tissue ingrowth to the portion of the frame that is disposed in the vicinity of the mitral annulus (e.g., at the mitral annulus, and/or slightly above the mitral annulus (e.g., as described hereinabove)) and is covered with skirt 48, and/or tissue ingrowth from the left atrium wall to the struts 46 of the frame (which, in some applications, are covered with sleeves 50). Typically, prior to the tissue ingrowth having occurred, the docking element is anchored in place within the left atrium by virtue of the frame expanding such as to contact the walls and the roof of the left atrium. For some applications, the frame is configured to only apply a relatively low pressure to the inner wall of the left atrium, such that the frame conforms to the shape of the left atrium, rather than forcing the atrium to deform. Typically, the shape of the frame changes over the course of the subject's cardiac cycle, as the shape of the subject's left atrium changes. For some applications, in this manner, the frame allows the natural compliance of the inner wall of the left atrium to be substantially maintained.

Typically, the expansion of the frame such as to contact the walls and the roof of the left atrium would not provide sufficient support to anchor the docking element in place within the left atrium, once the prosthetic mitral valve apparatus is placed inside the docking element, such that the docking element is exposed to left ventricular blood pressure being exerted upon the prosthetic mitral valve leaflets. Therefore, prior to the implantation of the prosthetic mitral valve apparatus, the docking element is left in place within the left atrium, such as to allow sufficient tissue ingrowth to occur, prior to implantation of the prosthetic mitral valve apparatus.

Typically, the docking element is configured such that, by the time that the prosthetic mitral valve apparatus is implanted, the anchoring of the docking element within the left atrium is primarily via the tissue ingrowth to the docking element. Typically, the mitral annulus is able to bear a higher load than other portions of the left atrial walls. Therefore, for some applications, the docking element is configured such that, when the prosthetic mitral valve apparatus is implanted, the anchoring of the docking element within the left atrium is primarily via the tissue ingrowth from the atrial walls in the vicinity of the mitral annulus to the docking element. For example, by virtue of the docking element including skirt 48 (which is configured to be disposed in the vicinity of the mitral annulus (e.g., at the mitral annulus, and/or slightly above the mitral annulus (e.g., as described hereinabove)), the docking element may be configured to encourage greater tissue ingrowth in the vicinity of the mitral annulus than at other portions of the frame.

The above-described, two-stage implantation procedure is somewhat analogous to a valve-in-valve procedure, whereby a new prosthetic valve is implanted inside a previously-implanted prosthetic valve. The previously-implanted prosthetic valve is typically initially anchored to the native mitral valve via suturing, but subsequently becomes anchored by virtue of tissue ingrowth to the prosthetic valve. In such cases, the new valve typically becomes anchored within the previously-implanted valve, and the previously-implanted valve is strongly anchored to the native mitral valve, by virtue of tissue ingrowth with respect to the previously-implanted valve, as well as mechanical force exerted upon the heart by the previously-implanted prosthetic valve. Similarly, in accordance with some applications of the present invention, initially, docking element 20 is implanted and is allowed to become anchored to the subject's heart by virtue of tissue ingrowth with respect to the docking element, as well as mechanical force exerted upon the heart by the docking element. Subsequently, once the docking element is anchored within the subject's heart, prosthetic mitral valve apparatus is anchored to the docking element. For some applications, stented frame 32 of prosthetic mitral valve apparatus 28 has an hourglass-shaped outer profile, that is configured to facilitate anchoring of the frame to ring 40 of docking element 20.

For some applications, the docking element and the prosthetic mitral valve apparatus are implanted above the native mitral valve in the same procedure as each other, with the docking element typically being implanted prior to the prosthetic mitral valve apparatus. For some such applications, when the prosthetic mitral valve apparatus is initially implanted, the prosthetic mitral valve leaflets are held open, for example, using sutures. Typically, the prosthetic mitral valve leaflets are maintained in the open state (e.g., using the sutures) for a period of more than more than one week, or more than one month, during which period the docking element becomes anchored to the subject's heart by virtue of tissue ingrowth, in accordance with the techniques described hereinabove. In this manner, during the period in which the docking element is becoming anchored to the subject's heart by virtue of tissue ingrowth, the docking element is not required to bear the load of blood impacting the prosthetic valve leaflets. Subsequently, the element that is keeping the prosthetic valve leaflets open (e.g., the sutures) is removed, such that the prosthetic valve leaflets begin functioning.

Typically, cells 45 defined by struts 46 of frame 24 are relatively large. For example, the cells may define open areas of more than 3.0 square cm (e.g., more than 4.0 square cm), and/or less than 6.0 square cm (e.g., less than 5.5 square cm), e.g., 3.0-6.0 square cm (or 4.0-5.5 square cm). For some applications the cells are disposed such that the open portions of the cells are disposed at junctions of the pulmonary veins with the left atrium. Typically, skirt 48 does not extend to a height upon the frame that is disposed junctions of the pulmonary veins with the left atrium. In this manner the frame does not interfere with blood flow from the pulmonary veins from to the left atrium.

In accordance with respective applications of the present invention, docking element 20 and/or prosthetic mitral valve apparatus 28 is delivered to the subject's heart via the femoral vein, transapically, transseptally, and/or transaortically. For some applications, by delivering docking element 20 and prosthetic mitral valve apparatus 28 in separate delivery steps, the size of the delivery device(s) that is/are used to deliver docking element 20 and prosthetic mitral valve apparatus 28 may be smaller than if the prosthetic mitral valve apparatus was to be delivered together with the docking element, ceteris paribus. For some applications, reducing the size of the delivery device(s) that is/are required, in the above-described manner, facilitates transseptal insertion of the docking element and/or the prosthetic mitral valve apparatus.

As described hereinabove, typically, docking element 20 is configured to facilitate anchoring of prosthetic mitral valve apparatus 28 to the subject's mitral valve. For some applications, the docking element occupies some of the area defined by the native mitral annulus. For example, it is typically the case that skirt 48 occupies some of the space between (a) the location at which the frame becomes anchored to the atrial walls in the vicinity of the native mitral annulus (by virtue of tissue ingrowth to the skirt and/or the frame itself) and (b) ring 40. That is to say that the docking element typically includes (a) ring 40 (within which the prosthetic valve apparatus is anchored), and (b) a portion of the frame that is covered with skirt 48, such as to encourage tissue ingrowth from the atrial walls in the vicinity of the mitral annulus to that portion. Typically, the size of the ring (e.g., the outer perimeter of the ring) is smaller than the size of the portion of the frame into which there is the tissue ingrowth (e.g., the inner perimeter of the portion of the frame). Further typically, there is a material (e.g., a fabric) that bridges between the ring and the portion of the frame into which there is the tissue ingrowth. For some applications, the material that bridges between the ring and the portion of the frame into which there is the tissue ingrowth is a portion of skirt 48.

In accordance with the above, for some applications, the size of the prosthetic mitral valve is smaller than that of the native mitral valve. For example, prosthetic valve leaflets 34 of the prosthetic mitral valve apparatus may span a diameter that is less than the measured diameter of the native mitral annulus (the diameter of the native mitral annulus typically being measured using a mitral measuring ring, and/or using imaging methods, such as ultrasound). Or, since the native mitral valve annulus is typically elliptical, the maximum diameter that is spanned by the leaflets may be less than the long axis of the ellipse defined by the native mitral valve annulus. For some applications, one or more advantages of the prosthetic valve being sized in this manner, relative to if the prosthetic valve were to be larger, may include: the prosthetic valve apparatus having a lower crimped profile (and therefore the use of a delivery device having a smaller diameter), there being less foreign matter inside the subject's heart, lower forces being exerted on the prosthetic valve leaflets (and therefore improved durability), better anchoring of the prosthetic valve apparatus, less interference with the native anatomy, and/or better preservation of a clear left ventricular outflow tract. Typically, smaller sized leaflets allow the frame of the prosthetic mitral valve apparatus to be shorter, thereby reducing obstruction of the left ventricular outflow tract, ceteris paribus. Alternatively or additionally, prosthetic mitral valve apparatus having prosthetic valve leaflets spanning a diameter that is less than that of the native mitral annulus may be used for a different reason.

Typically, the prosthetic mitral valve apparatus becomes anchored within ring 40 of docking element 20. Typically, the inner diameter of ring 40 is more than 20 mm. For some applications, the inner diameter of ring 40 is smaller than the inner diameter of native mitral annulus 44. For example, the inner diameter of ring 40 may be less than 30 mm, e.g., less than 28 mm. As described hereinabove, for some applications, the docking element occupies some of the area defined by the native mitral annulus. For example, it is typically the case that skirt 48 occupies some of the space between where the frame becomes anchored to the native mitral annulus (by virtue of tissue ingrowth to the skirt and/or the frame itself) and ring 40. In this manner, the ring acts as an artificial mitral annulus that is smaller than the native mitral annulus. Typically, for such applications, the prosthetic mitral valve is configured to have a diameter that is less than the native mitral valve. For example, a ratio of the diameter of the prosthetic mitral valve to the diameter (or the long axis) of the native mitral valve may be less than 7:8, or less than 3:4. For some applications, the prosthetic mitral valve has a diameter that is less than that of the native mitral valve, and has an effective orifice area of 1.8 cm^2 or more, which is typically sufficiently large for the heart to function healthily, in the majority of patients.

Figure 2:
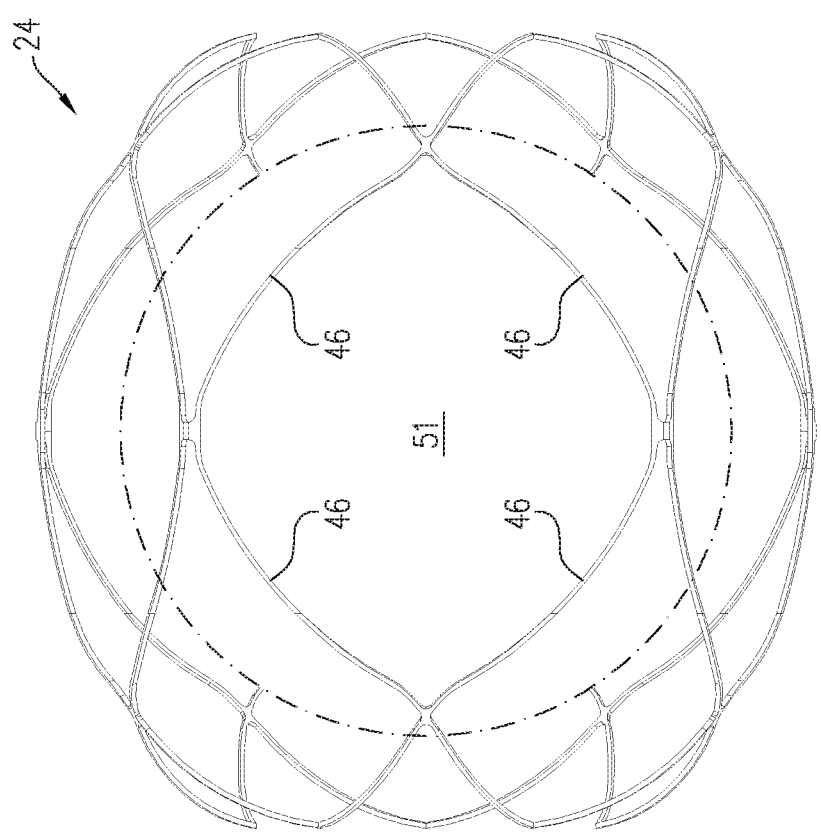
FIG. 2 is a schematic illustration of a cross-sectional view of a frame of a docking element, in accordance with some applications of the present invention.

Reference is now made to FIG. 2 is a schematic illustration of a cross-sectional view of frame 24 of docking element 20, in accordance with some applications of the present invention. The dashed circle in FIG. 2 indicates where the frame has been cut in order to generate the cross-sectional view that is shown. As shown, the frame typically defines a cell 51 that is configured to be disposed at the side of the frame that is placed in the vicinity of the mitral annulus. For some applications, cell 51 defines an open area of more than 3.0 square cm (e.g., more than 4.0 square cm), and/or less than 6.0 square cm (e.g., less than 5.5 square cm), e.g., 3.0-6.0 square cm (or 4.0-5.5 square cm). Typically, ring 40 (not shown in FIG. 2) is disposed inside cell 51. Further typically, skirt 48 covers any space between struts that define cell 51 and ring 40, such as to seal this space. For some applications, the skirt additional covers spaces (or portions thereof) defined by additional cells. For some applications, ring 40 is directly coupled to the struts that define cell 51 (e.g., as shown in FIGS. 4A-B). Alternatively, the ring is coupled to the struts that define cell 51 via skirt 48. For example, skirt 48 may be stitched to both the struts that define cell 51, and to ring 40 (e.g., as shown in FIGS. 3A-B).

Typically, prior to the tissue ingrowth having occurred the docking element is anchored in place within the left atrium by virtue of the frame expanding such as to contact the walls and the roof of the left atrium. For some applications, the frame is configured to only apply a relatively low pressure to the inner wall of the left atrium, such that the frame conforms to the shape of the left atrium, rather than forcing the atrium to deform. For some applications, in this manner, the frame allows the natural compliance of the inner wall of the left atrium to be substantially maintained. For example, the frame may be configured such that 1N of force is required for a reduction in diameter of the frame of 10 mm. For some applications, each of the cells of the frame defines an open area of more than 3.0 square cm (e.g., more than 4.0 square cm), and/or less than 6.0 square cm (e.g., less than 5.5 square cm), e.g., 3.0-6.0 square cm (or 4.0-5.5 square cm). It is noted that frame 24 is typically configured such that contact between the frame and left atrium is spread substantially evenly over the walls of the left atrium and roof of the left atrium. It is further noted that, typically, the frame does not include any additional anchoring portions for anchoring to body portions (such as the left atrial appendage and/or pulmonary veins), other than the walls and the roof of the left atrium.

Typically, the expansion of the frame such as to contact the walls and the roof of the left atrium would not provide sufficient support to anchor the docking element in place within the left atrium once the prosthetic mitral valve is placed inside the docking element, such that the docking element is exposed to left ventricular blood pressure being exerted upon the prosthetic mitral valve leaflets. Therefore, prior to the implantation of the prosthetic mitral valve apparatus, the docking element is left in place within the left atrium, such as to allow sufficient tissue ingrowth to occur, prior to implantation of the prosthetic mitral valve apparatus. Typically, the docking element is configured such that, when the prosthetic mitral valve apparatus is implanted, the anchoring of the docking element within the left atrium is primarily via the tissue ingrowth to the docking element. Typically, the mitral annulus is able to bear a higher load than other portions of the left atrial walls. Therefore, for some applications, the docking element is configured such that, when the prosthetic mitral valve apparatus is implanted, the anchoring of the docking element within the left atrium is primarily via the tissue ingrowth from the atrial walls in the vicinity of the mitral annulus to the docking element. For some applications, skirt 48 is configured to be disposed at least partially in the vicinity of the mitral annulus (e.g., at the mitral annulus and/or slightly above the mitral annulus (e.g., as described hereinabove)) in order to promote tissue ingrowth from the atrial walls in the vicinity of the mitral annulus to the frame.

Figure 3A:
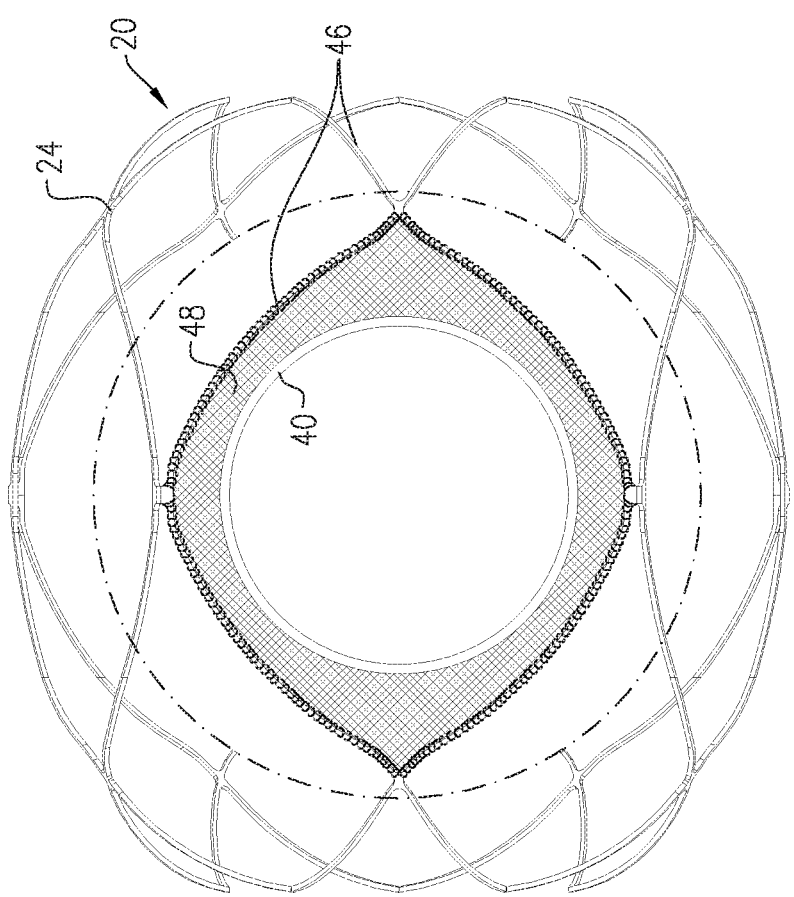
FIGS. 3A, 3B, and 3C are schematic illustrations of a docking element configured to facilitate anchoring of prosthetic mitral valve apparatus to a subject's mitral valve, in accordance with some applications of the present invention.
Figure 3B:
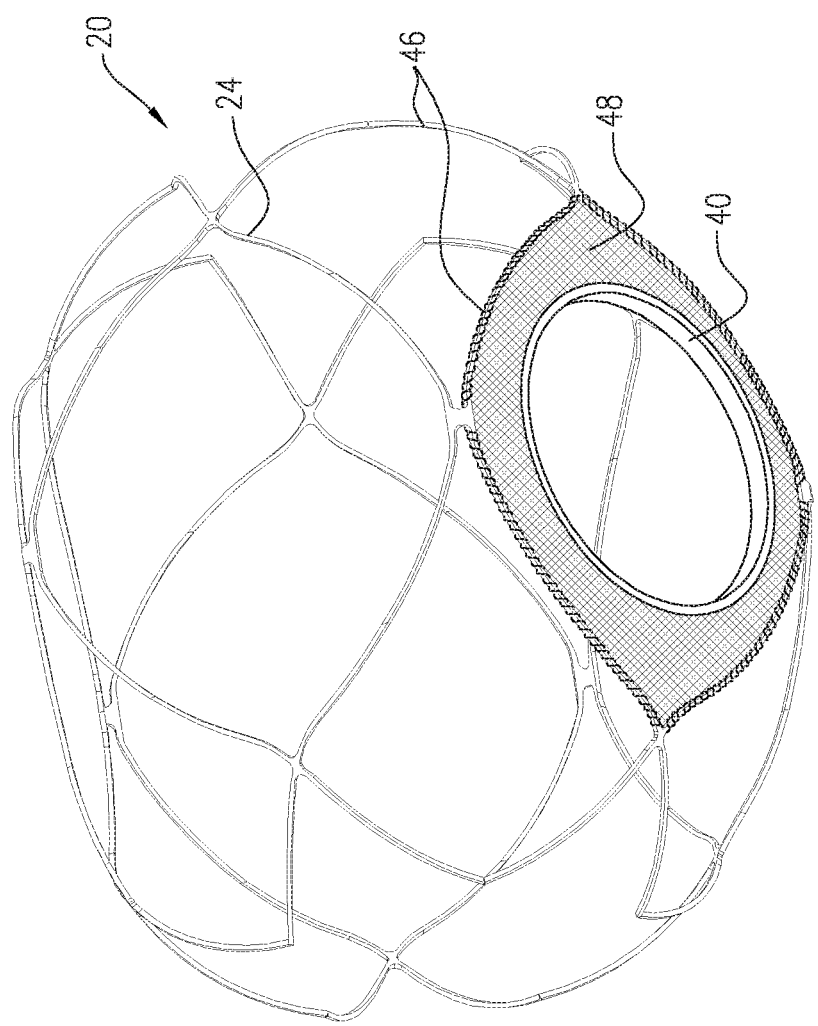
Figure 3C:
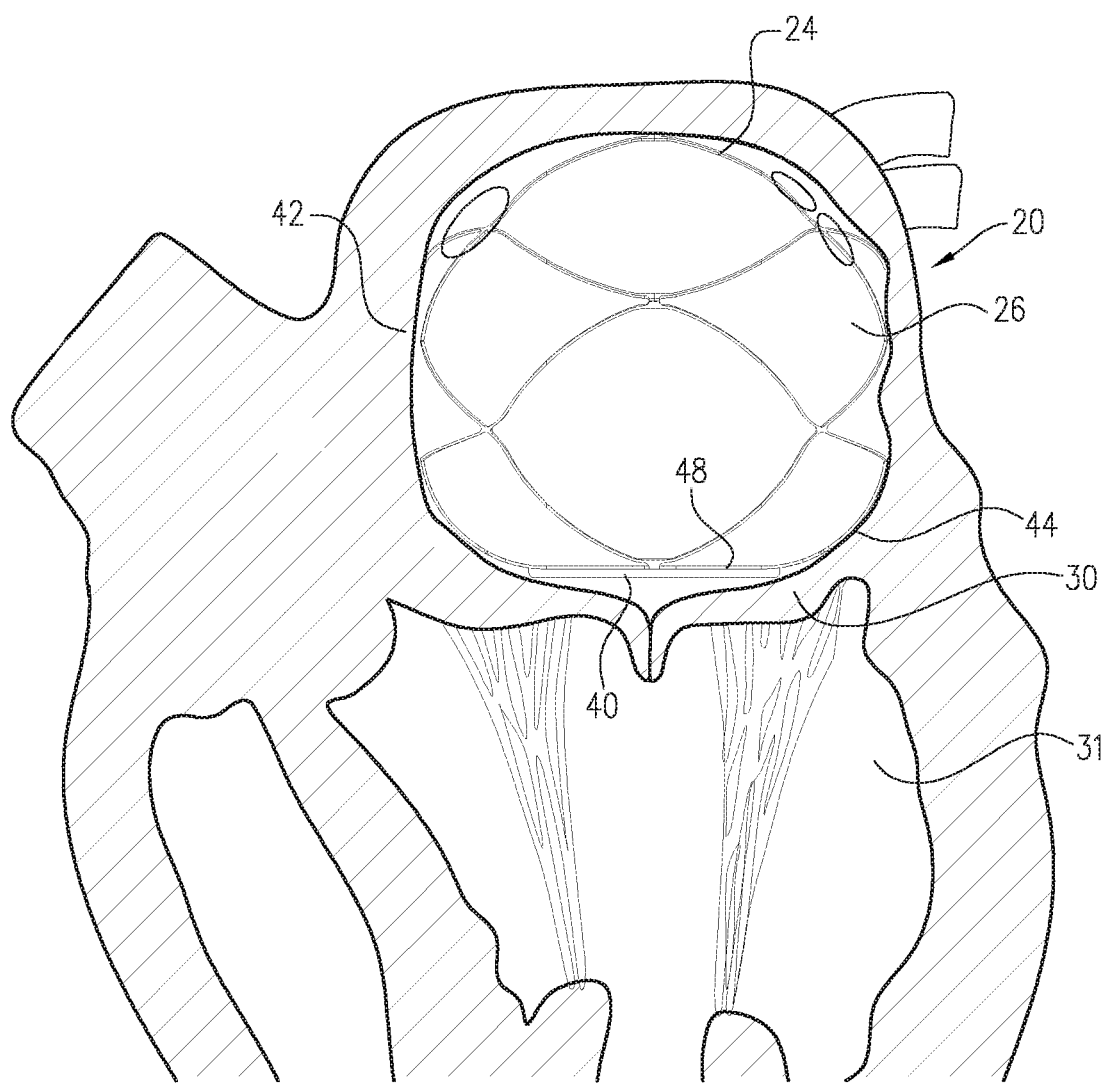
Figure 4A:
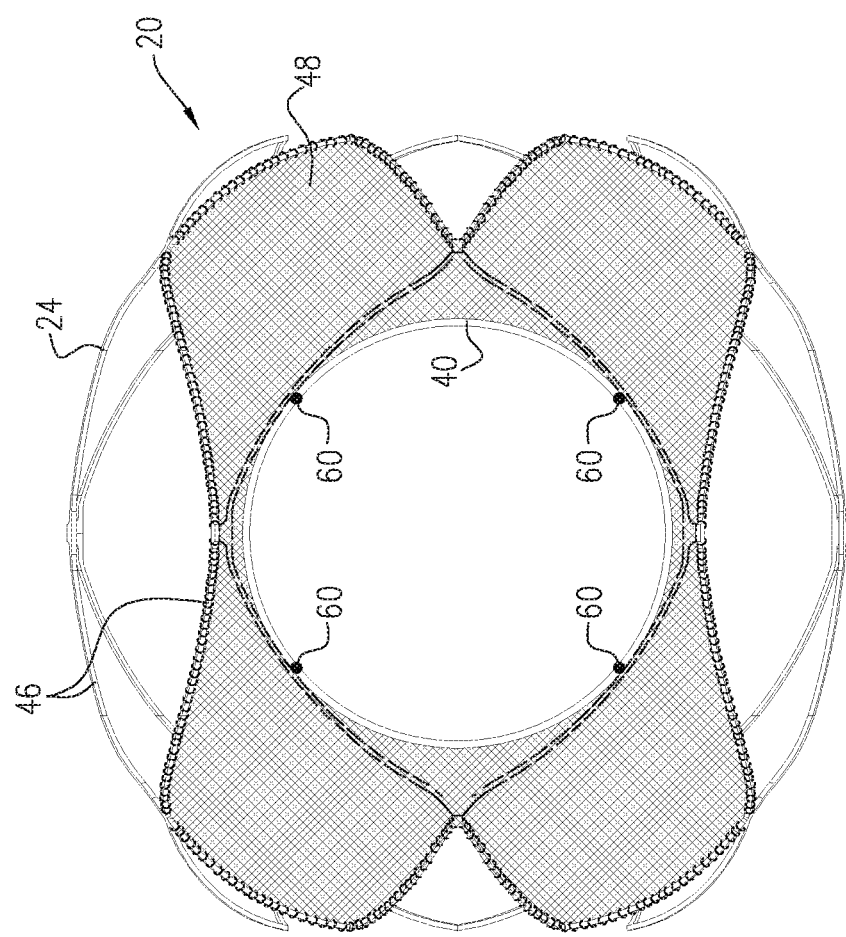
FIGS. 4A, 4B, and 4C are schematic illustrations of a docking element configured to facilitate anchoring of prosthetic mitral valve apparatus to a subject's mitral valve, in accordance with some applications of the present invention.
Figure 4B:
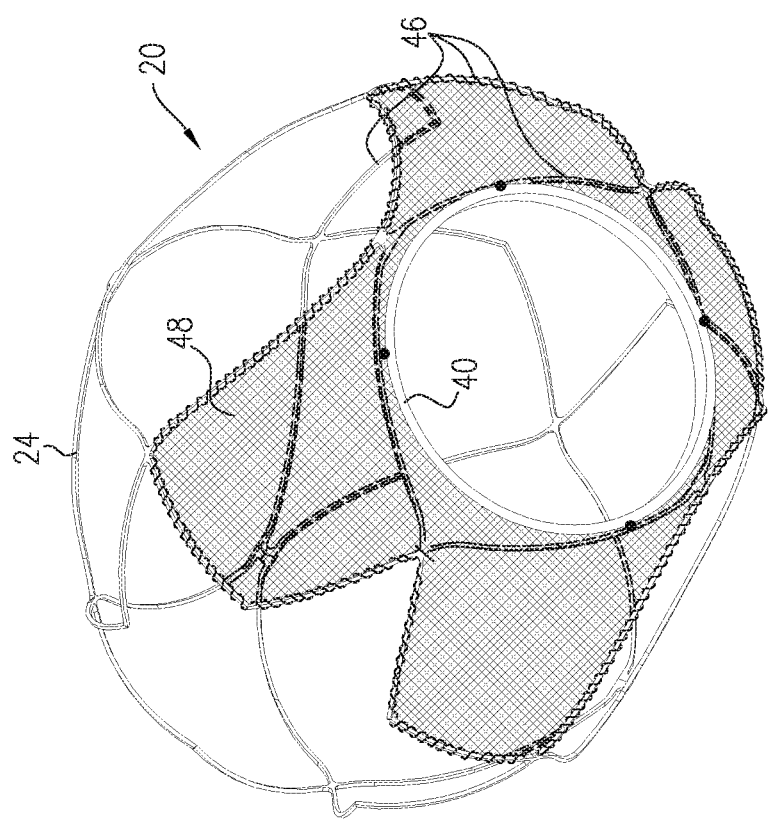

Reference is now made to FIGS. 3A, 3B, and 3C, which are schematic illustrations of docking element 20, which is configured to facilitate anchoring of prosthetic mitral valve apparatus 28 (FIG. 1A) to a subject's mitral valve, in accordance with some applications of the present invention. FIG. 3A shows a cross-sectional view of the docking element, the dashed circle in FIG. 3A indicating where the frame has been cut in order to generate the cross-sectional view that is shown. FIG. 3B shows a three-dimensional view of the docking element. FIG. 3C shows the docking element disposed within a subject's left atrium, prior to the prosthetic mitral valve apparatus being deployed. As noted hereinabove, for some applications, ring 40 is coupled to the struts that define cell 51 (shown in FIG. 2) via skirt 48. For example, skirt 48 may be stitched to both the struts that define cell 51, and to ring 40. An example of a frame in accordance with such applications is shown in FIGS. 3A-B. As shown, skirt 48 fills any space between struts that define cell 51, and ring 40, such as to seal this space.

Referring to FIG. 3C, for some applications, the inner diameter of ring 40 is smaller than the inner diameter of native mitral annulus 44. For example, the inner diameter of ring 40 may be less than 30 mm, e.g., less than 28 mm. As described hereinabove, for some applications, the docking element occupies some of the area defined by the native mitral annulus. (It is noted that for the configuration of the skirt shown in FIGS. 3A and 3B, the skirt is not visible in the view of the docking element that is shown in FIG. 3C.) For example, it is typically the case that skirt 48 occupies the space between where the frame becomes anchored to the atrial walls in the vicinity of the native mitral annulus (by virtue of tissue ingrowth to the skirt and/or the frame itself) and ring 40. Further typically, the skirt seals the space between where the frame becomes anchored to the native mitral annulus and ring 40. In this manner, the ring acts as an artificial mitral annulus that is smaller than the native mitral annulus.

Figure 3D:
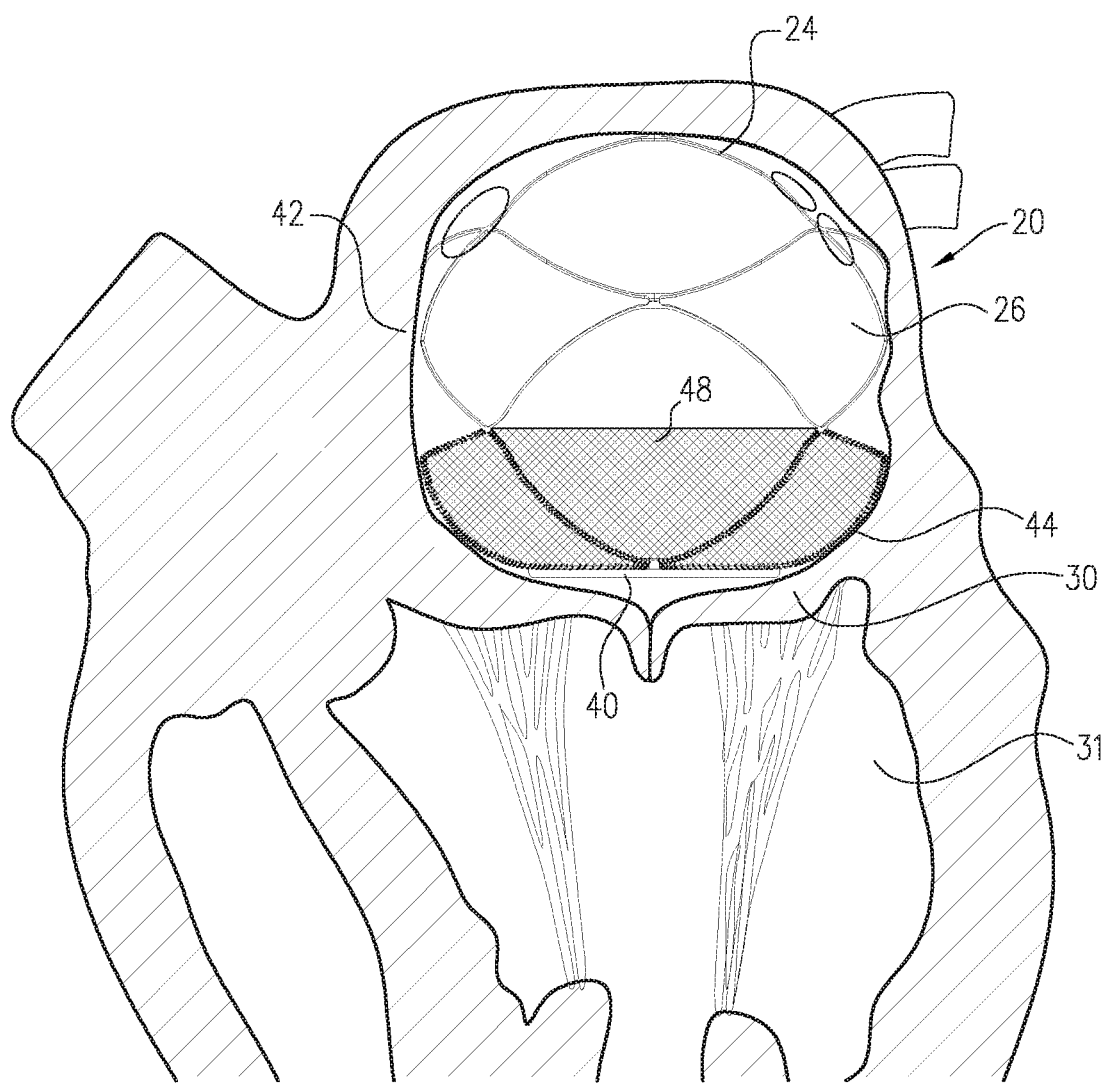
FIGS. 3D and 3E are schematic illustrations of a docking element, with a skirt of the docking element being sutured to the frame in a different manner to that shown in FIGS. 3A-C, in accordance with some applications of the present invention.
Figure 3E:
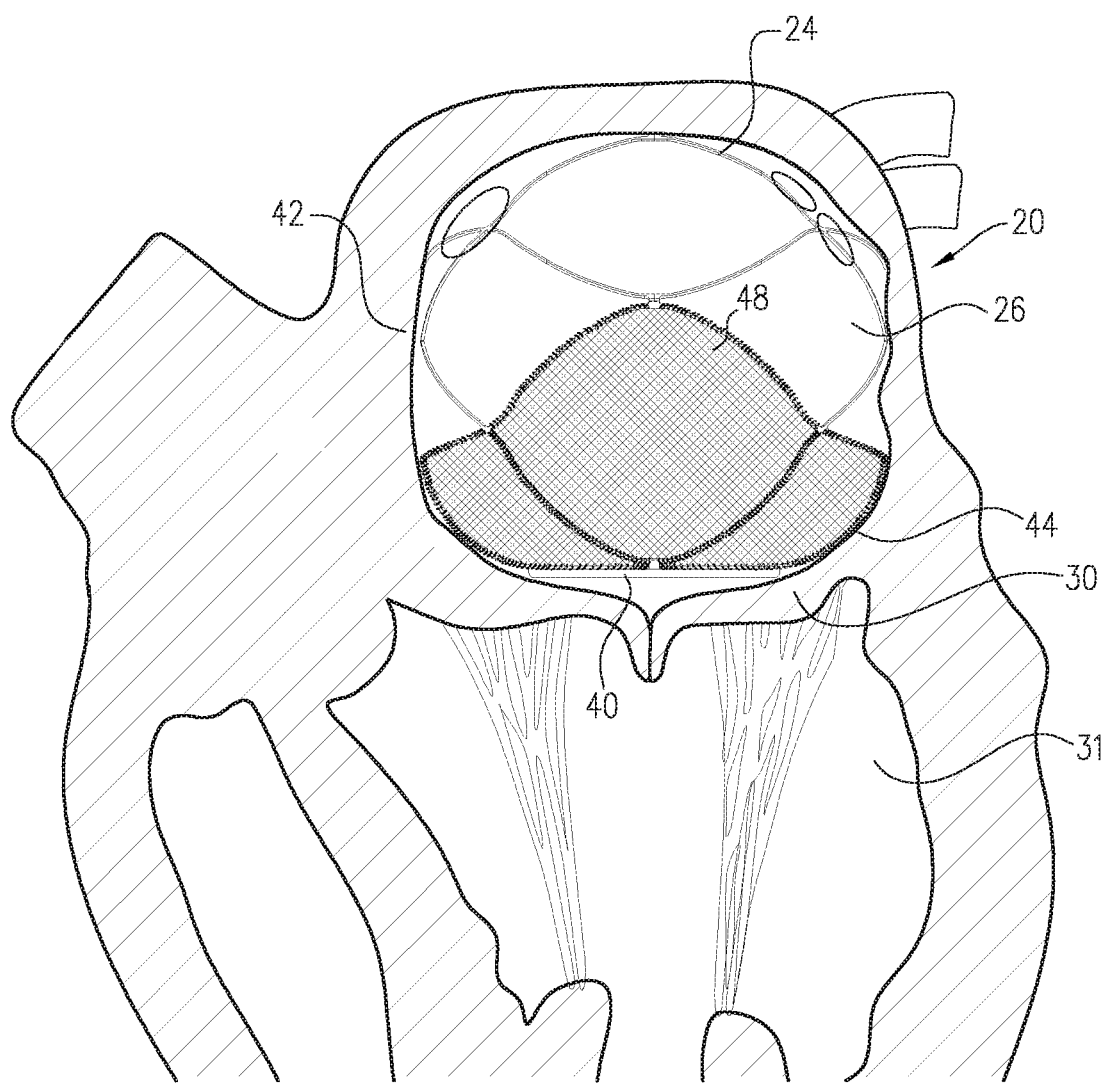

Reference is now made to FIGS. 3D and 3E, which are schematic illustrations of docking element 20, with skirt 48 being sutured to the frame in a different manner to that shown in FIGS. 3A-C, in accordance with some applications of the present invention. In all other aspects, the frame as shown in FIGS. 3D and 3E is generally similar to that described with reference to FIGS. 3A-C.

Figure 4C:
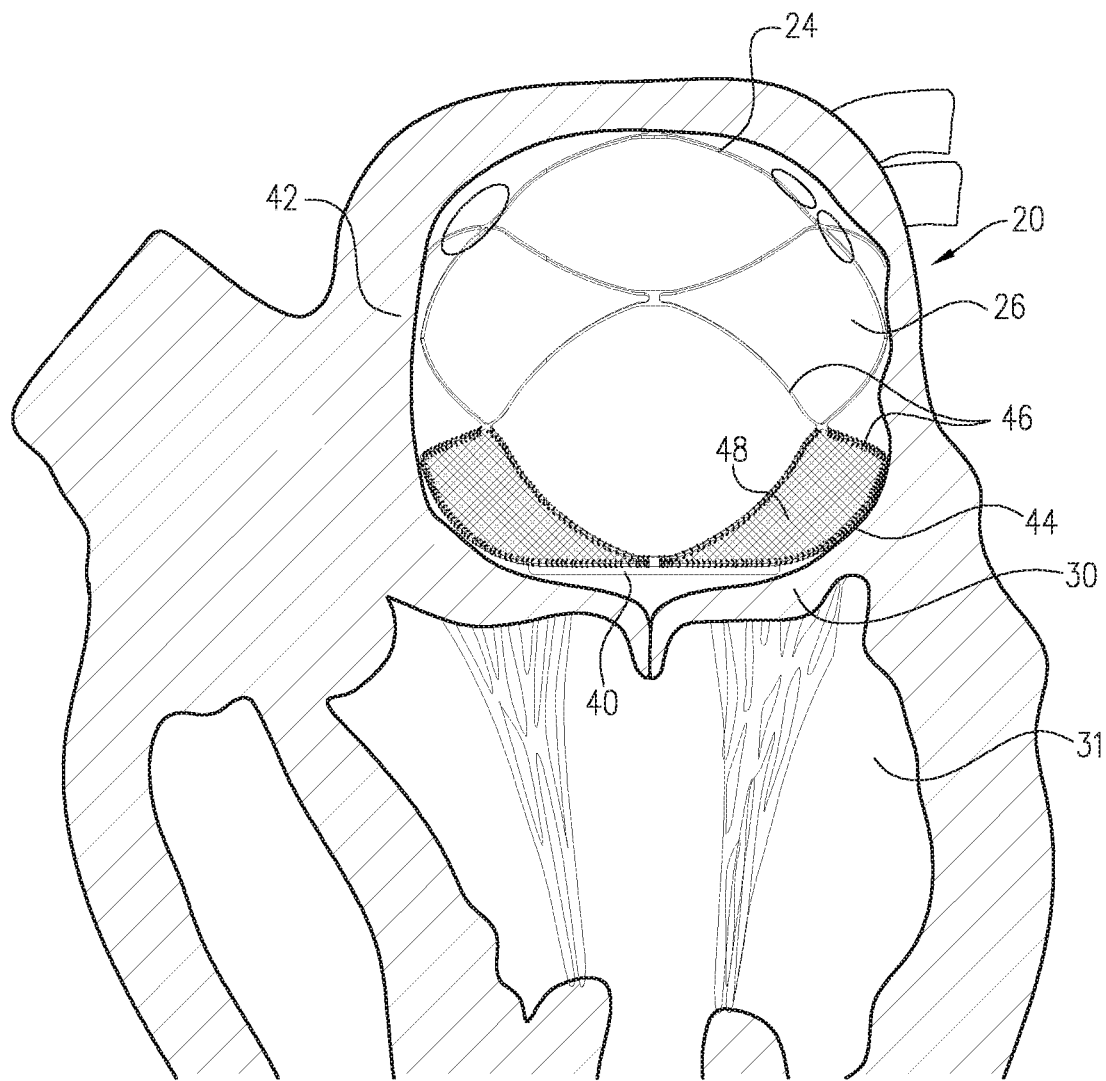

Reference is now made to FIGS. 4A, 4B, and 4C, which are schematic illustrations of docking element 20, which is configured to facilitate anchoring of prosthetic mitral valve apparatus 28 (FIG. 1A) to a subject's mitral valve, in accordance with some applications of the present invention. FIG. 4A shows a view of the docking element from below ring 40. FIG. 3B shows a three-dimensional view of the docking element. FIG. 4C shows the docking element disposed within a subject's left atrium, prior to the prosthetic mitral valve apparatus being deployed. As noted hereinabove, for some applications, ring 40 is directly coupled to the struts that define cell 51 (shown in FIG. 2). For example, skirt 48 may be welded to the struts that define cell 51 at welding points 60 (shown in FIG. 4A). An example of a frame in accordance with such applications is shown in FIGS. 4A-C. Typically, skirt 48 fills any space between struts that define cell 51, and ring 40, such as to seal this space.

Referring to FIG. 4C, for some applications, the inner diameter of ring 40 is smaller than the inner diameter of native mitral annulus 44. For example, the inner diameter of ring 40 may be less than 30 mm, e.g., less than 28 mm. As described hereinabove, for some applications, the docking element occupies some of the area defined by the native mitral annulus. For example, it is typically the case that skirt 48 occupies the space between where the frame becomes anchored to the atrial walls in the vicinity of the native mitral annulus (by virtue of tissue ingrowth to the skirt and/or the frame itself) and ring 40. Further typically, the skirt seals the space between where the frame becomes anchored to the atrial walls in the vicinity of the native mitral annulus and ring 40. In this manner, the ring acts as an artificial mitral annulus that is smaller than the native mitral annulus.

Figure 4D:
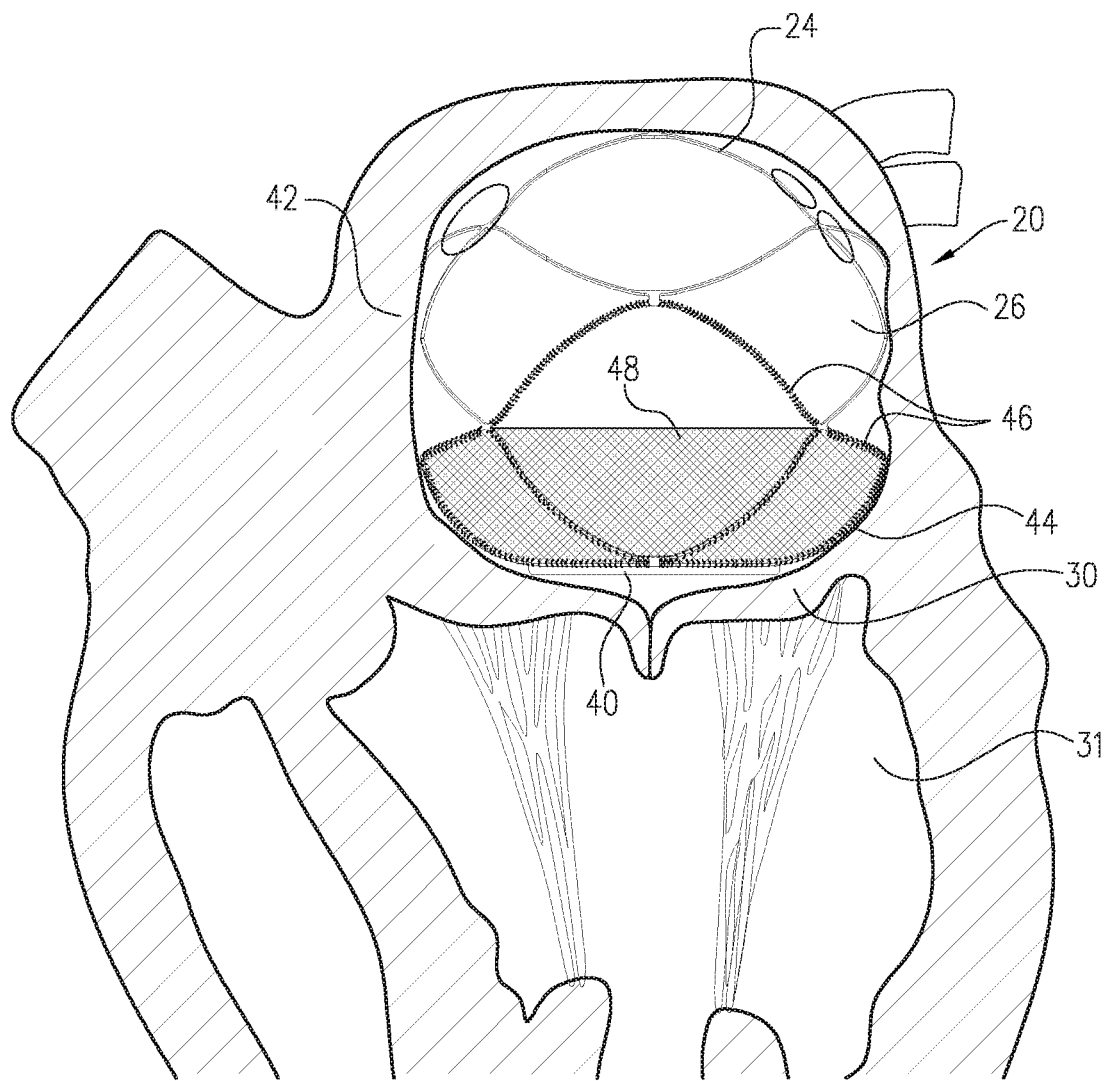
FIGS. 4D and 4E are schematic illustrations of a docking element, with a skirt of the docking element being sutured to the frame in a different manner to that shown in FIGS. 4A-C, in accordance with some applications of the present invention.
Figure 4E:
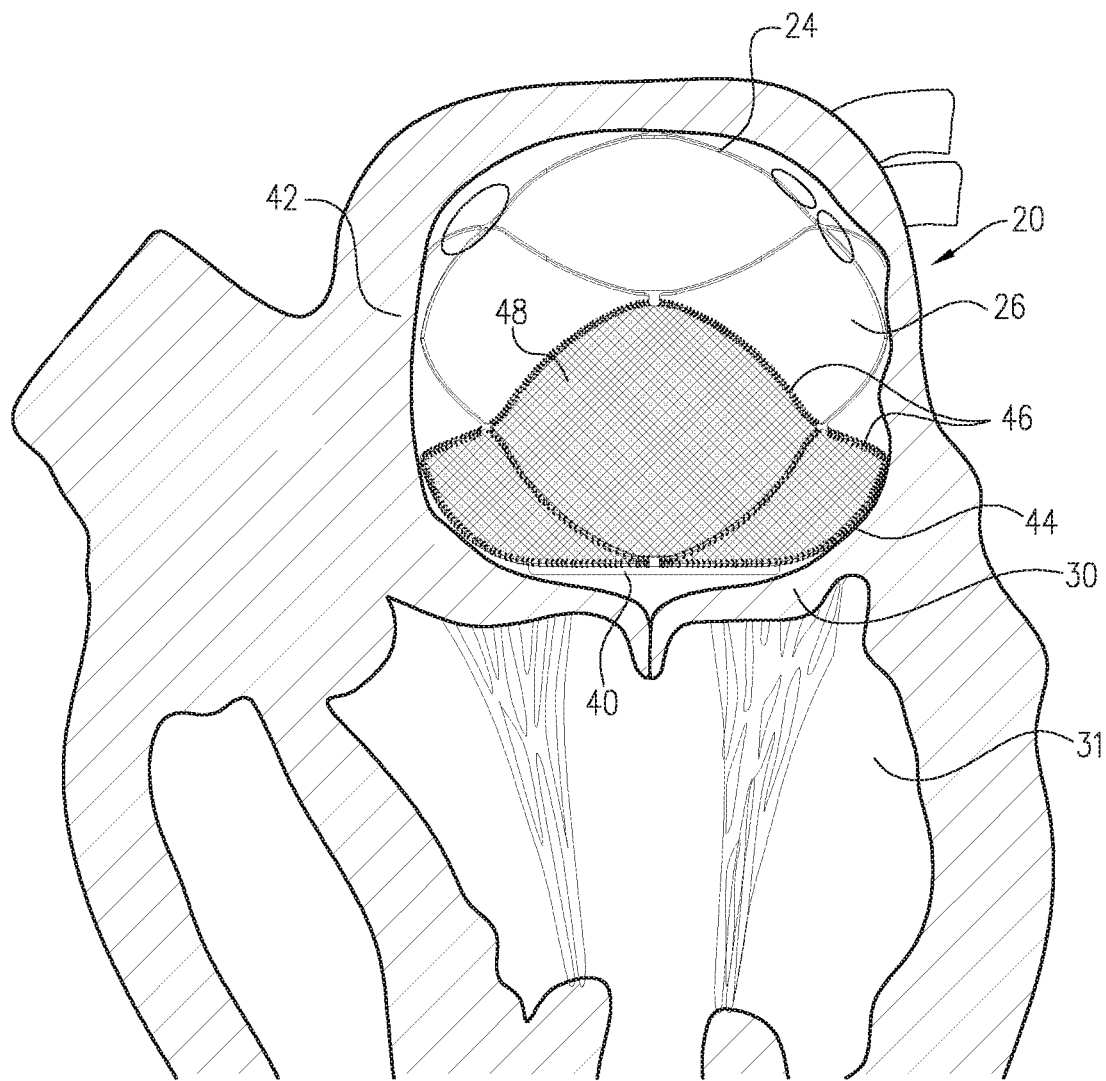

Reference is now made to FIGS. 4D and 4E, which are schematic illustrations of docking element 20, with skirt 48 being sutured to the frame in a different manner to that shown in FIGS. 4A-C, in accordance with some applications of the present invention. In all other aspects, the frame as shown in FIGS. 4D and 4E is generally similar to that described with reference to FIGS. 4A-C It is noted that, although FIGS. 1A-C show sleeves 50 disposed around struts 46 of frame 24, for some applications, struts of the frame are not covered with sleeves. Examples of such applications are shown in FIGS. 3A-4E.

Figure 5A:
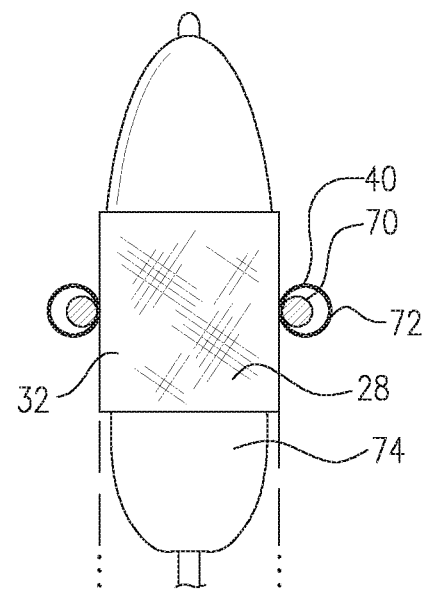
FIGS. 5A, 5B, and 5C show respective steps of a frame of a prosthetic mitral valve apparatus being expanded by a balloon inside a ring of a docking element, in accordance with some applications of the present invention.
Figure 5B:
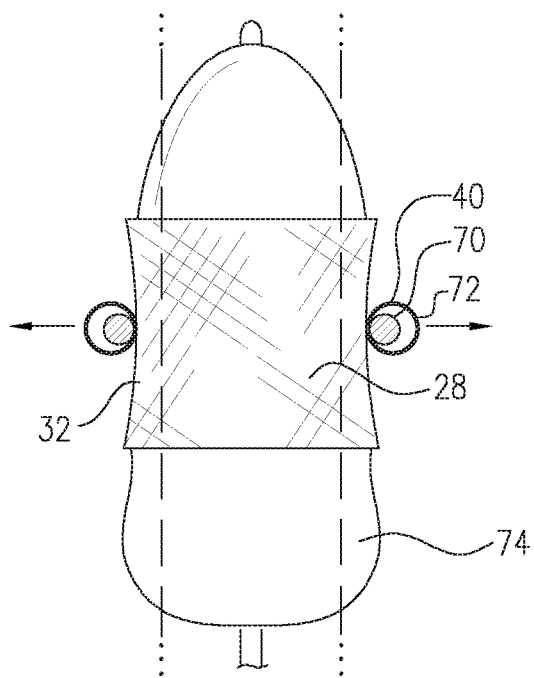
Figure 5C:
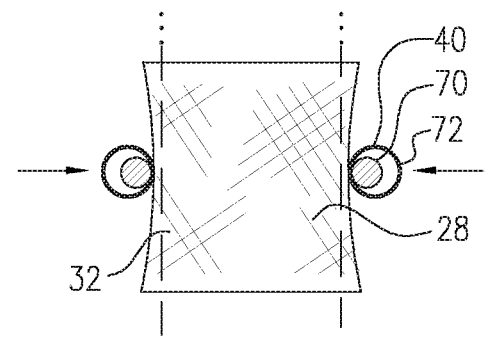

Reference is now made to FIGS. 5A-C, which shows respective steps of frame 32 of prosthetic mitral valve apparatus 28 being expanded by a balloon 74 inside ring 40 of docking element 20, in accordance with some applications of the present invention. (As described in further detail hereinbelow, for some applications, ring 40 includes a hollow torus 72 and an inner ring 70, which are shown in FIGS. 5A-C.) Subsequent to tissue ingrowth occurring and the prosthetic mitral valve apparatus being deployed, ring 40 is configured to apply radial forces on the frame of the prosthetic mitral valve apparatus, in order to anchor the prosthetic mitral valve apparatus, even when strong forces are applied to the prosthetic mitral valve apparatus (e.g., during ventricular systole). Typically, the prosthetic mitral valve apparatus is delivered to the native mitral valve via a delivery device, while in a radially-constrained configuration. For some applications, the prosthetic mitral valve apparatus is configured to radially self-expand upon being released from the delivery device. Alternatively, the prosthetic mitral valve apparatus is configured to be expanded by balloon 74, for example, using balloon expansion techniques that are known in the art. For example, frame 32 of the prosthetic mitral valve apparatus may be made of a metal such as stainless steel or cobalt chromium.

Typically, in cases in which the prosthetic mitral valve apparatus is balloon expandable, frame 32 of the prosthetic mitral valve apparatus is expanded to a given diameter due to the balloon inflation, but then undergoes a slight recoil subsequent to the balloon being deflated, due to the elastic properties of frame 32 and/or due to ring 40 radially compressing the frame. This is shown in the transition from FIG. 5A to FIG. 5B, and then to FIG. 5C. Since the prosthetic mitral valve is expanded inside ring 40, the ring is typically configured to:

(a) define a given diameter when it is not subjected to any forces, (b) expand to a second diameter to allow the balloon-expanded prosthetic mitral valve apparatus to open to its maximum diameter, as shown in FIG. 5B, (c) undergo a reduction in diameter that is at least similar to the reduction in diameter that the prosthetic mitral valve apparatus undergoes during its recoil (which is typically in the range of 1 percent to 10 percent, e.g., 2 percent to 6 percent), as shown FIG. 5C, and (d) after undergoing the changes in diameter, exert sufficient radial force on the prosthetic mitral valve apparatus to anchor it in place even during left ventricular systole.

Figure 6A:
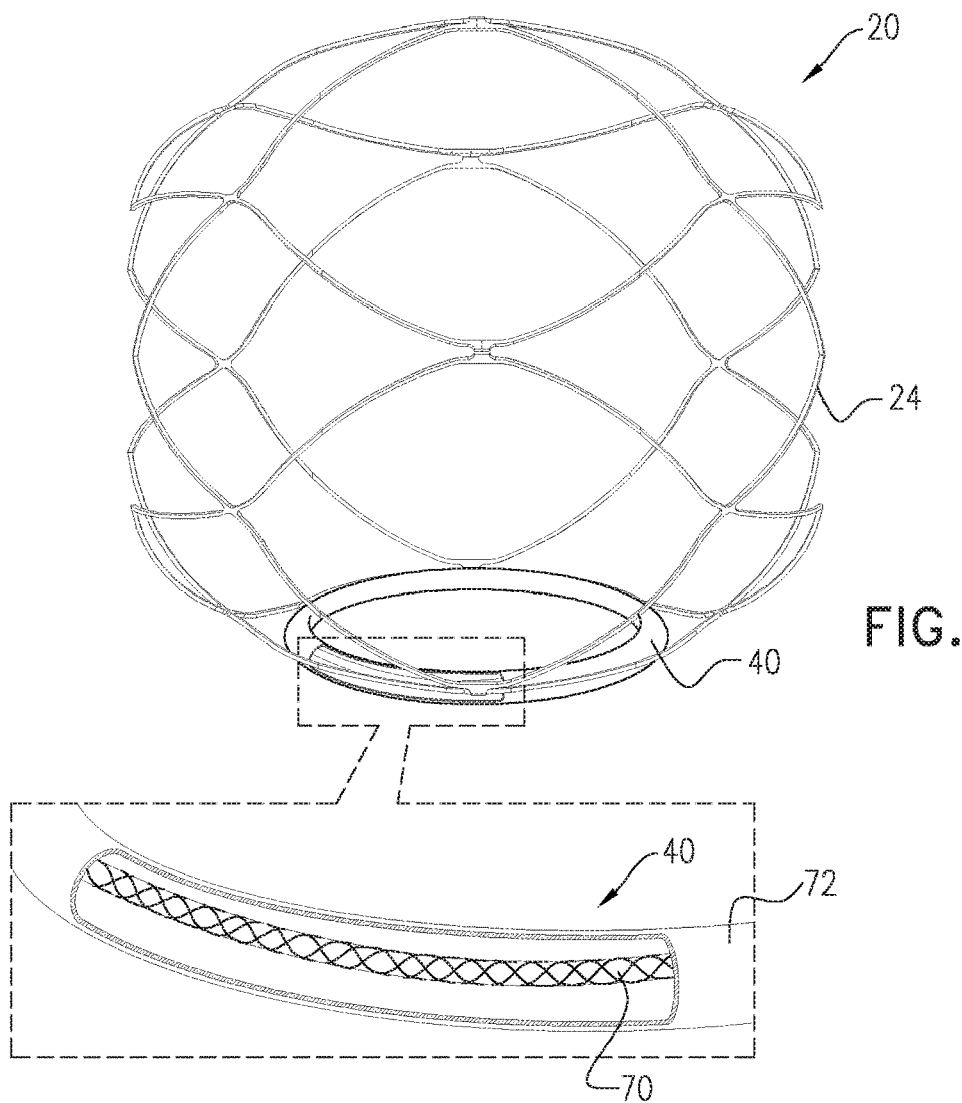
FIG. 6A is a schematic illustration of a docking element, in accordance with some applications of the present invention.
Figure 6B:
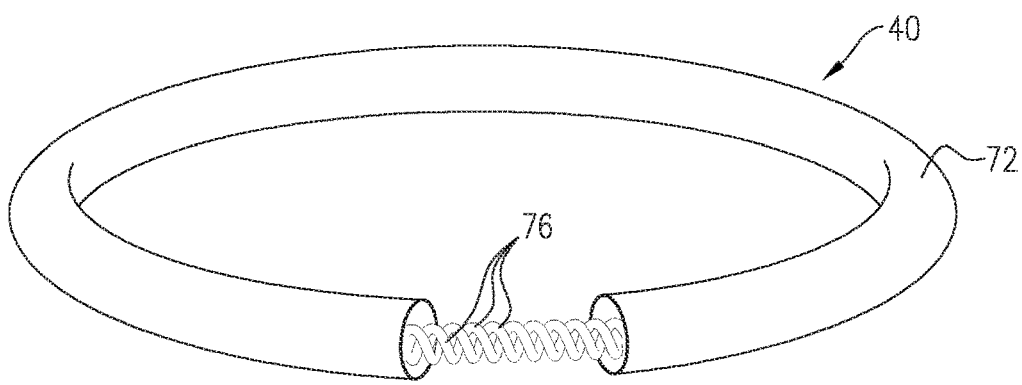
FIG. 6B is a schematic illustration of a ring of a docking element, in accordance with some applications of the present invention.

Reference is now made to FIG. 6A, which is a schematic illustration of docking element 20, in accordance with some applications of the present invention. It is noted that the docking element is shown in FIG. 6A in the absence of skirt 48, for illustrative purposes. Reference is also made to FIG. 6B, which is a schematic illustration of ring 40, in accordance with some applications of the present invention.

For some applications, ring 40 includes a hollow torus 72, (which is typically made of a fabric, such as PET, PTFE, and/or nylon), and an inner ring 70. The inner ring is typically made of an elastic material having the above-described characteristics (i.e., characteristics (a)-(d) listed above). For example, as shown in FIG. 6A, the inner ring may be made of a polymeric material, suture material, rubber, and/or a super-elastic, metallic material designed or cut in a such a way as to provide the above-described characteristics. Alternatively or additionally, the inner ring may include a spring made of one or more wires 76, which function as an elastic ring with the above-described characteristics, as shown in FIG. 6B. For some applications, the inner ring has a similar configuration to spring 102 shown in FIGS. 9A-B, and/or to spring 120 shown in FIGS. 11A-C.

Figure 7:
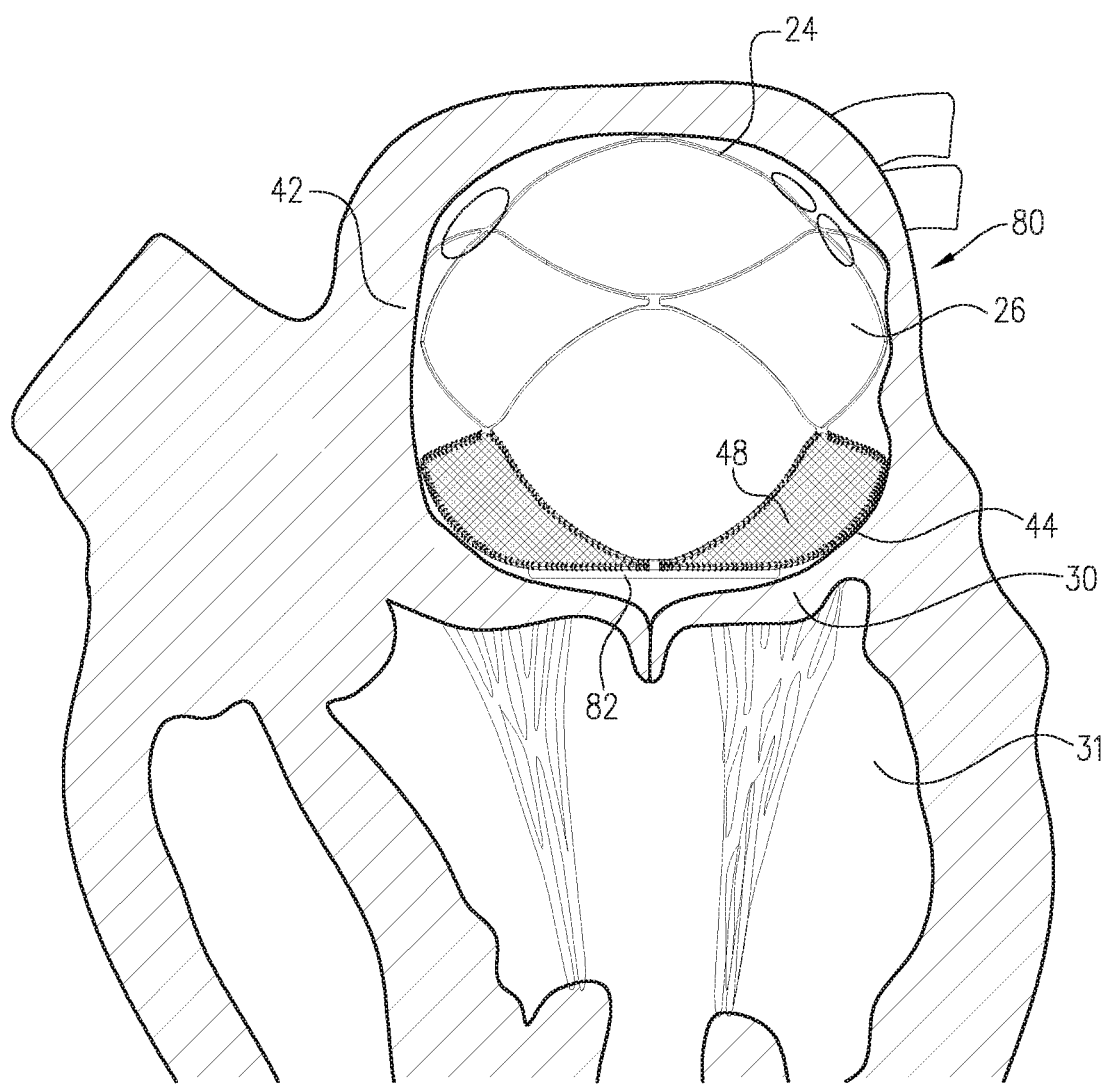
FIG. 7 is a schematic illustration of a mitral annulus repair device, in accordance with some applications of the present invention.

Reference is now made to FIG. 7, which is a schematic illustration of a mitral annulus repair device 80, in accordance with some applications of the present invention. Typically, mitral annulus repair device 80 is implanted in a subject suffering from mitral valve regurgitation, in which there is backflow of blood from the left ventricle to the left atrium during systole, due to the mitral valve leaflets not fully closing.

Typically, mitral annulus repair device 80 is generally similar to docking element 20, except for differences described hereinbelow. Similar reference numerals are used for components of the mitral annulus repair device that are similar to components of docking element 20. As shown, many of the components of the mitral annulus repair device are similar to components of docking element 20. However, for some applications, in place of ring 40 (which is configured to anchor a prosthetic mitral valve apparatus), mitral annulus repair device includes an adjustable or self-adjusting ring 82. Rather than being used to support a prosthetic mitral valve apparatus, adjustable ring 82 is configured to decrease the area of the mitral annulus, by the diameter of the ring decreasing by being adjusted (e.g., via cinching), or self-adjusting, subsequent to tissue ingrowth having occurred, as described hereinbelow with reference to FIGS. 8A-11C. It is noted that although the configuration of the frame and skirt of mitral annulus repair device 80 is similar to that of docking element 20 as shown in FIGS. 4A-C, the scope of the present invention includes using any of the configurations of frame 24 and/or skirt 48 described hereinabove with reference to docking element 20 within mitral annulus repair device 80. For example, any of the configurations of the frame and skirt shown in FIGS. 1A-C, 3A-E, and/or 4A-E may be used.

Typically, prior to the diameter of ring 82 decreasing, mitral annulus repair device 80 is left in place within the left atrium, such as to allow tissue ingrowth to occur. Typically, the mitral annulus repair device is configured such that, when the diameter of the ring is decreased, the anchoring of the mitral annulus repair device within the left atrium is primarily via the tissue ingrowth to the mitral annulus repair device. For some applications, the mitral annulus repair device is configured such that, when the diameter of the ring is decreased, the anchoring of the mitral annulus repair device within the left atrium is primarily via the tissue ingrowth from the atrial walls in the vicinity of the mitral annulus to the mitral annulus repair device. For example, by virtue of the mitral annulus repair device including skirt 48 (which is configured to be disposed in the vicinity of the mitral annulus, e.g., at the mitral annulus or slightly above the mitral annulus (e.g., as described hereinabove)), the mitral annulus repair device may be configured to encourage greater tissue ingrowth from the atrial walls in the vicinity of the mitral annulus than at other portions of the frame.

Typically, once sufficient tissue ingrowth has occurred, the diameter of the ring is decreased by being adjusted (e.g., via cinching), or self-adjusting. Typically, since the atrial walls in the vicinity of the mitral annulus has undergone tissue ingrowth with respect to the mitral annulus repair device, decreasing the diameter of the ring remodels the heart, by reducing the size of the mitral annulus. In turn, the mitral leaflets are brought closer to each other and mitral valve regurgitation is reduced or eliminated. It is noted that, for some applications, there isn't substantial tissue ingrowth with respect to ring 82. Rather, most of the tissue ingrowth is with respect to frame 24. Nevertheless, since the ring is coupled to the frame and there is tissue ingrowth from the atrial walls in the vicinity of the mitral annulus with respect to the frame, the reduction in the diameter of the ring causes a reduction in the size of the mitral annulus.

Figure 8A:
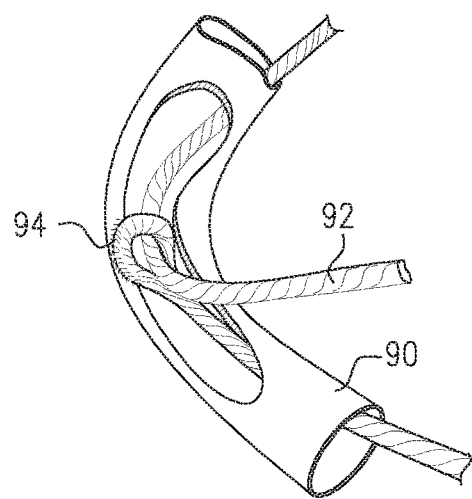
FIGS. 8A, 8B, and 8C are schematic illustrations of a ring of a mitral annulus repair device, in accordance with some applications of the present invention.
Figure 8B:
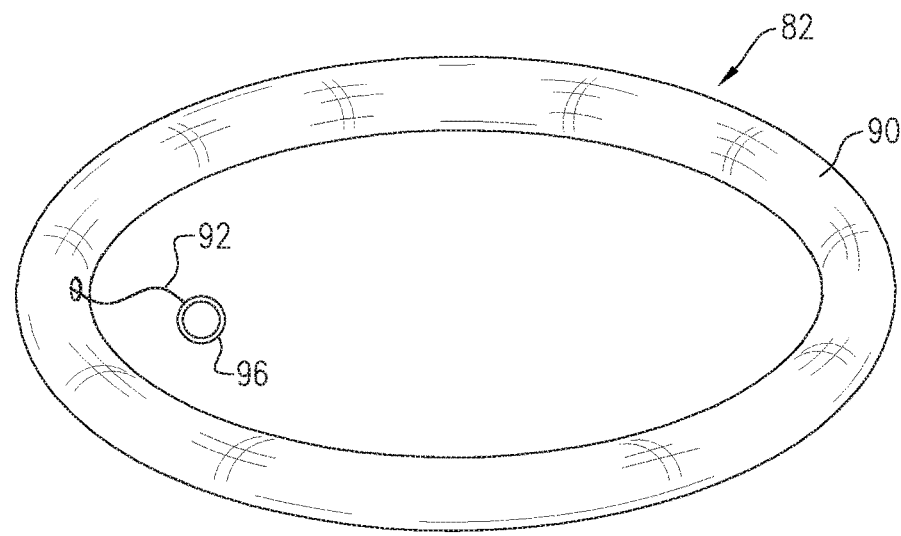
Figure 8C:
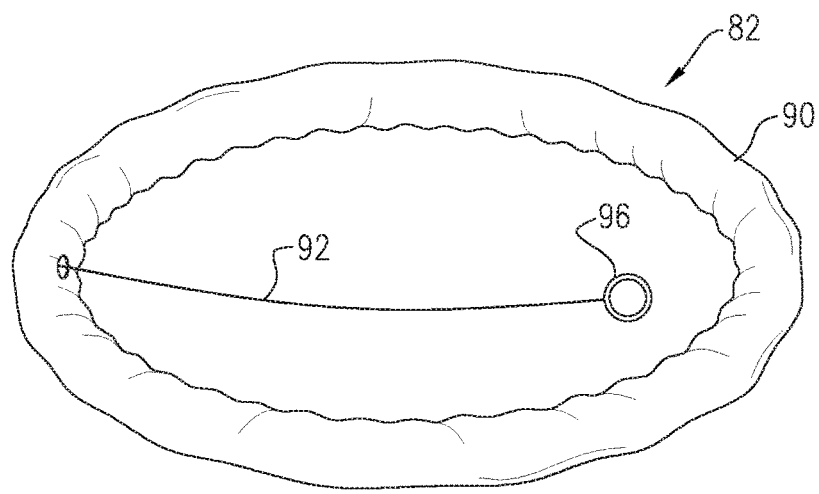

Reference is now made to FIGS. 8A-C, which are schematic illustrations of ring 82 of mitral annulus repair device 80, in accordance with some applications of the present invention. (FIGS. 8A-C show the ring in the absence of frame 24, but the ring is typically coupled to the frame, as shown in FIG. 7.) For some applications, ring 82 includes a hollow torus 90, (which is typically made of a fabric, such as PET, PTFE, and/or nylon), and a string 92 threaded through the torus. The string is typically attached to the torus at a first end 94 (e.g., via stitching), and the second end 96 of the string is free. Typically the torus is coupled to frame 24 of the mitral annulus repair device (e.g., via stitching). The second end of the string is typically pulled by an operator, which causes the diameter of the ring to decrease, as shown in the transition from FIG. 8B to FIG. 8C. This in turn decreases the size of the mitral annulus, as described hereinabove. For some applications (not shown), both ends of the string protrude from the torus, and both ends of the string are pulled (like a drawstring), by an operator, in order to decrease the diameter of the ring. Typically, once the diameter of the ring has been reduced to a desired diameter, the end(s) of string are tied in order to fix the ring at this diameter. Alternatively or additionally, the ring may include a ratchet mechanism (or a similar mechanism, not shown) in order to fix the diameter of the ring.

Figure 9A:
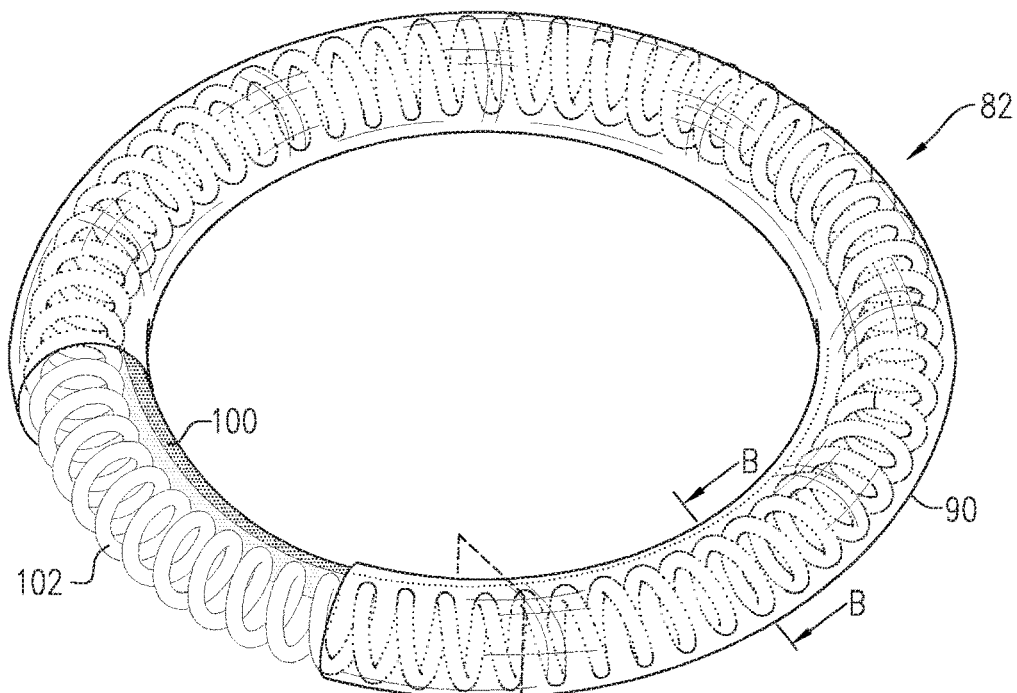
FIGS. 9A and 9B are schematic illustrations of a ring of a mitral annulus repair device, in accordance with some applications of the present invention.
Figure 9A:
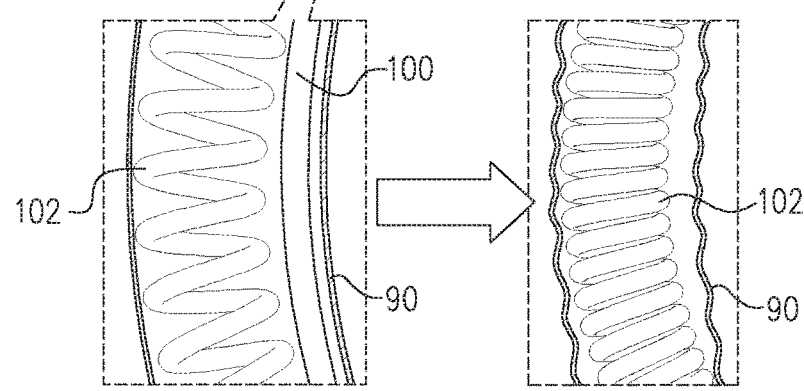
Figure 9B:
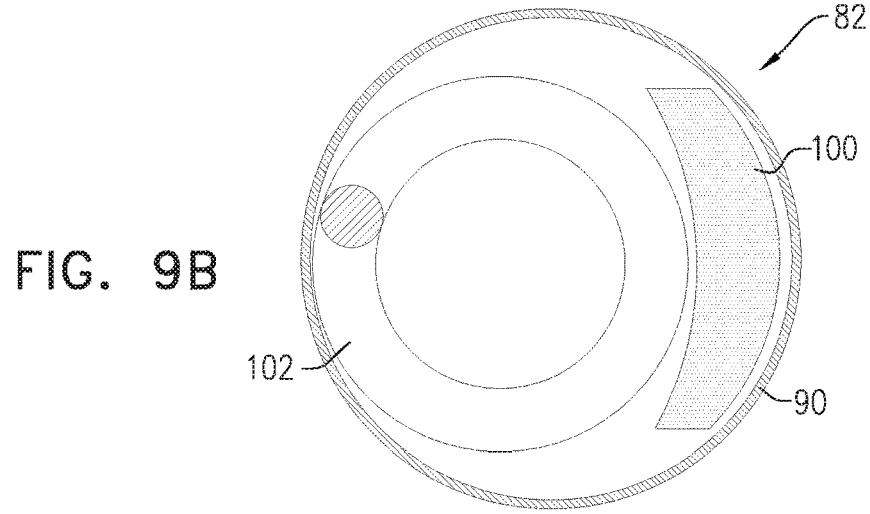

Reference is now made to FIGS. 9A-B, which are schematic illustrations of ring 82 of mitral annulus repair device 80, in accordance with some applications of the present invention. (FIGS. 9A-B show the ring in the absence of frame 24, but the ring is typically coupled to the frame, as shown in FIG. 7.) FIG. 9B shows a cross-sectional view of the ring. For some applications, ring 82 includes hollow torus 90, which is generally as described with reference to FIGS. 8A-C. For some applications, a biodegradable ring 100 made of a biodegradable material (such as polylactide and/or polyglycolide), having a first diameter or cord length is disposed within the hollow torus. For some applications, a spring 102 is disposed within the torus and around the biodegradable ring, such as to apply an inward radial force to the biodegradable ring. Typically, after a certain time period (by which time tissue ingrowth, as described hereinabove, will have occurred), the biodegradable ring becomes degraded and the radial forces of the spring exert an inward force on the torus causing the diameter of ring 82 to decrease. This, in turn, decreases the size of the mitral annulus, as described hereinabove. The transition of ring 82 (from its configuration before ring 100 has become degraded to after ring 100 has become degraded) is indicated in the cross-sectional views of the ring that are shown in FIG. 9A.

Figure 10A:
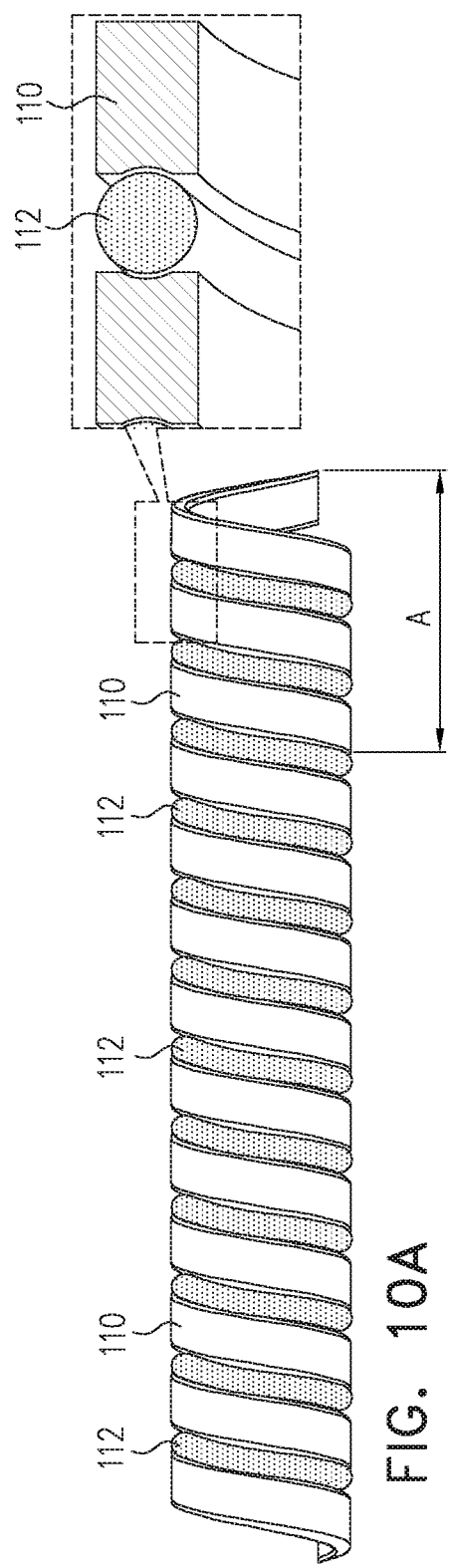
FIGS. 10A and 10B are schematic illustrations of an inner component of a ring of a mitral annulus repair device, in accordance with some applications of the present invention.
Figure 10B:
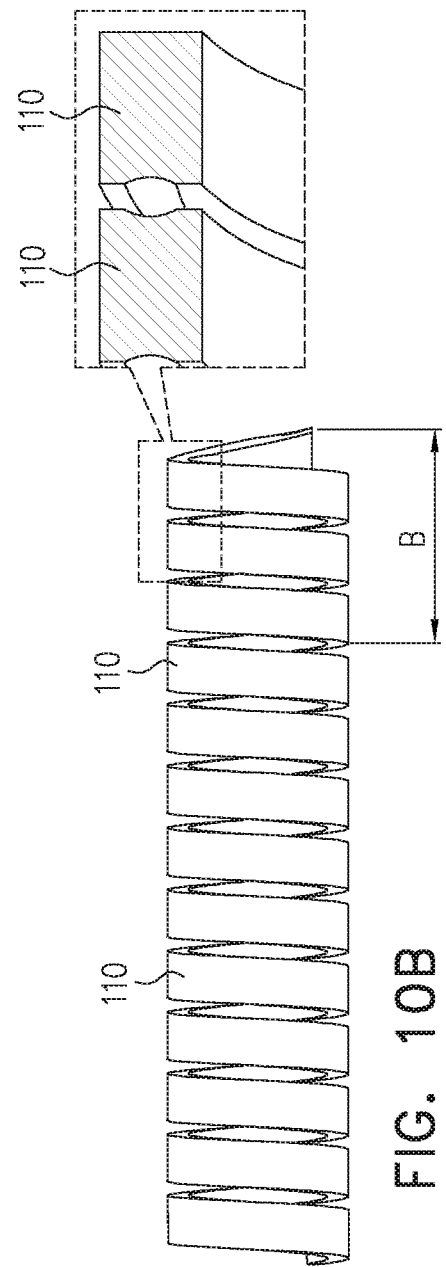

Reference is now made to FIGS. 10A-C, which are schematic illustrations of an inner component of ring 82 of mitral annulus repair device 80, in accordance with some applications of the present invention. For some applications, ring 82 includes a hollow torus 90 (not shown in FIGS. 10A-C), which is generally as described with reference to FIG. 8A-C, and the inner component shown in FIGS. 10A-C disposed inside the hollow torus. For some applications, a spring 110 is disposed within the torus. The spring is initially held open by a biodegradable material 112 (such as polylactide and/or polyglycolide), which is disposed between windings of the spring, thereby forcing the spring to stay open. Typically, after a certain time period (by which time tissue ingrowth, as described hereinabove, will have occurred), the biodegradable material dissolves and the spring closes (as shown in the transition from FIG. 10A to FIG. 10B). Radial forces of the spring exert an inward force on the torus causing the diameter of ring 192 to decrease. This, in turn, decreases the size of the mitral annulus, as described hereinabove.

Figure 11A:
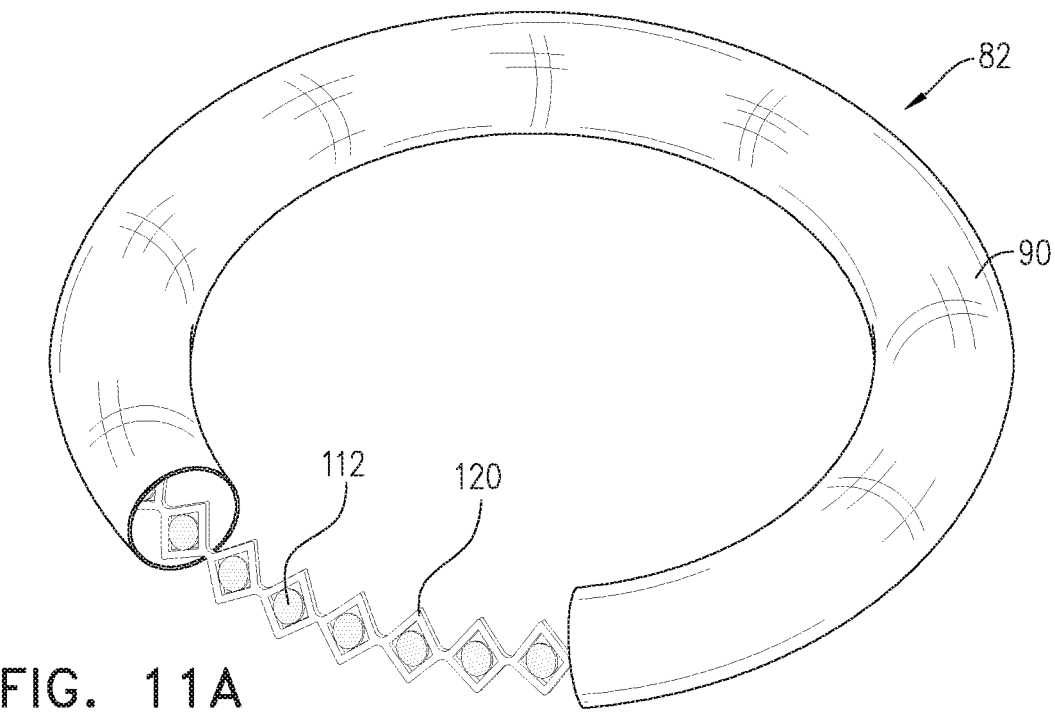
FIGS. 11A, 11B, and 11C are schematic illustrations of a ring of a mitral annulus repair device and components thereof, in accordance with some alternative applications of the present invention.
Figure 11B:
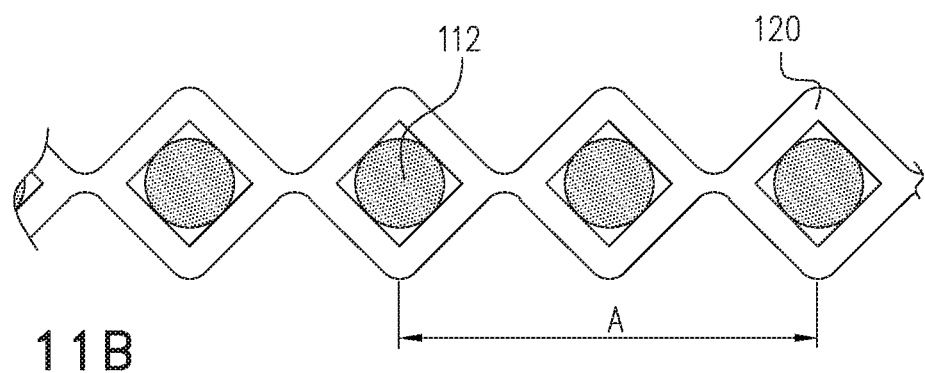
Figure 11C:
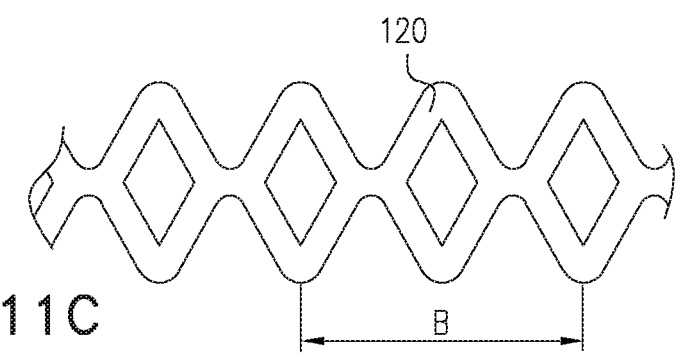

Reference is now made to FIGS. 11A-C, which are schematic illustrations of ring 82 of mitral annulus repair device 80 and components thereof, in accordance with some applications of the present invention. (FIG. 11A shows the ring in the absence of frame 24, but the ring is typically coupled to the frame, as shown in FIG. 7. FIGS. 11B and 11C show an inner component of the ring in the absence of outer torus 90, for illustrative purposes.) Ring 82 as shown in FIGS. 11A-C is generally similar to that shown and described with reference to FIGS. 10A-C. However the ring shown in FIGS. 11A-C, includes a spring 120 that is made of a self-expandable, shape memory material (e.g., a shape memory alloy, such as nitinol) that is prevented from assuming a small diameter configuration, into which it has been shape set, by virtue of biodegradable material 112. Typically, after a certain time period (by which time tissue ingrowth, as described hereinabove, will have occurred), the biodegradable material dissolves and the shape memory material assumes the smaller diameter configuration (as shown in the transition from FIG. 11B to 11C). Radial forces of the spring exert an inward force on the torus causing the diameter of ring 82 to decrease. This, in turn, decreases the size of the mitral annulus, as described hereinabove.

For some applications, a mitral annulus device that includes an adjustable ring (as described hereinabove with reference to FIGS. 7-11C) is used in conjunction with prosthetic mitral valve apparatus 28. For example, techniques that are generally as described with reference to FIGS. 1A-6B may be performed, but the diameter of the ring may be adjusted such as to accommodate a prosthetic mitral valve apparatus having a given desired diameter.

For some applications, the apparatus and methods described herein are performed with respect to a tricuspid valve, and/or a different valve in a subject's body, mutatis mutandis.

For some applications, the apparatus and methods described herein are performed in conjunction with apparatus and methods described in International Patent Application No. PCT/IL2018/050229 to Benichou et al. (published as WO 18/178966), entitled "Docking element," filed Mar. 1, 2018, which claims priority from U.S. Provisional Application 62/476,989 to Benichou, entitled "Docking element," filed Mar. 27, 2017, which is incorporated herein by reference.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An apparatus for treating a subject with a diseased mitral valve, the apparatus comprising:
    a docking element configured to be implanted within a left atrium of the subject such that no portion of the docking element extends through the subject's mitral valve, the docking element comprising:
        a ring configured to be implanted within 15 mm of a native mitral annulus of the subject, a size of the ring being smaller than a size of the subject's native mitral annulus;
        a frame extending from the ring,
            a portion of the frame being configured to be disposed radially outside of the ring in a vicinity of the subject's native mitral annulus and to generate tissue ingrowth to the docking element from atrial walls of the subject at least in the vicinity of the subject's native mitral annulus, and
            the frame being configured to anchor the docking element within the left atrium, prior to the tissue ingrowth to the docking element occurring, by the frame expanding against inner walls and a roof of the left atrium; and a material disposed between the portion of the frame and the ring, the material being configured to form a seal between the atrial walls in the vicinity of the native mitral annulus and the ring; and a prosthetic mitral valve apparatus configured:
subsequent to the ingrowth of the tissue of the left atrium to the portion of the frame having occurred, to be placed at least partially inside the docking element, and
to become anchored to the docking element, at least partially by radially expanding against the ring.

2. The apparatus according to claim 1, wherein the frame does not include additional anchoring portions for anchoring to any additional portions of the subject's body other than the walls and the roof of the left atrium.

3. The apparatus according to claim 1, wherein the ring comprises an outer portion that comprises a fabric hollow torus, and an inner portion that comprises an element selected from the group consisting of: an elastic material, and a spring.

4. The apparatus according to claim 1, wherein the ring is configured to be adjustable in size.

5. The apparatus according to claim 1, wherein the apparatus is for use with a balloon, wherein the prosthetic mitral valve apparatus comprises a balloon-expandable prosthetic mitral valve apparatus configured to be radially expanded by the balloon, and wherein the ring comprises an elastic ring that is configured:
to define a given diameter when the ring is not subjected to any forces,
to expand to a second diameter to allow the balloon-expandable prosthetic mitral valve apparatus to be expanded by the balloon,
to undergo a reduction in diameter that is at least similar to a reduction in diameter that the prosthetic mitral valve apparatus undergoes due to recoiling after the balloon is deflated, and after undergoing the expansion and reduction in diameter, to exert sufficient radial force on the prosthetic mitral valve apparatus to anchor it in place during left ventricular systole.

6. The apparatus according to claim 1, wherein the frame comprises a plurality of struts that define a plurality of cells, and wherein the material comprises a fabric skirt that is configured to cover a portion of the frame extending from the ring until a height of at least 5 mm from the ring.

7. The apparatus according to claim 6, wherein, when the frame is in a deployed state inside the left atrium, the cells are configured to define open areas of at least 3 square cm.

8. The apparatus according to claim 1, wherein the ring is configured to automatically adjust its size.

9. The apparatus according to claim 8, wherein the ring comprises a fabric hollow torus, with a spring and a biodegradable material dispose therein such that the biodegradable material holds the spring in an expanded configuration, and wherein the ring is configured to be automatically adjustable in size by the biodegradable material becoming degraded, and radial forces of the spring exerting a radially inward force on the torus.

10. The apparatus according to claim 1, wherein:
the docking element is configured to be placed into the subject's left atrium, via an interatrial septum of the subject, by advancing the docking element in a lateral direction with respect to the left atrium, along a longitudinal axis of the frame; and
the ring is disposed laterally with respect to the frame, such that the ring is substantially parallel with the longitudinal axis of the frame.

11. The apparatus according to claim 10, wherein the docking element is configured to be deployed within the subject's left atrium, such that the longitudinal axis of the frame is substantially parallel to the subject's native mitral annulus.

12. The apparatus according to claim 1, wherein the frame comprises a plurality of struts that define a plurality of cells, and wherein, within at least a portion of the frame, the struts of the frame are covered with fabric sleeves.

13. The apparatus according to claim 12, wherein at junctions between the struts that are covered with the fabric sleeves, adjacent fabric sleeves are stitched to each other.

14. A method for treating a subject with a diseased mitral valve, the method comprising:
inserting a docking element into a left atrium of the subject, the docking element including a ring, and a frame extending from the ring;
deploying the docking element within the subject's left atrium, such that:
no portion of the docking element extends through the subject's mitral valve,
the ring is disposed within 15 mm of a native mitral valve annulus of the subject,
a size of the ring is smaller than a size of the native mitral annulus,
a portion of the frame is disposed radially outside of the ring in a vicinity of the native mitral annulus of the subject, and the portion of the frame is configured to generate tissue ingrowth to the docking element from atrial walls of the subject at least in the vicinity of the subject's native mitral annulus,
the frame anchors the docking element within the left atrium, prior to the tissue ingrowth to the docking element occurring, by the frame expanding against the atrial walls and a roof of the left atrium, and
a material is disposed between the portion of the frame and the ring, the material being configured to form a seal between atrial walls in the vicinity of the native mitral annulus and the ring;
subsequent to the ingrowth of the tissue of the left atrium to the portion of the frame having occurred, inserting a prosthetic mitral valve apparatus inside the ring; and
causing the prosthetic mitral valve apparatus to radially expand against the ring, such that the prosthetic mitral valve apparatus is anchored within the ring.

* * * * *